United States Patent [19]
Black et al.

[11] Patent Number: 5,691,374
[45] Date of Patent: Nov. 25, 1997

[54] DIARYL-5-OXYGENATED-2-(5H)-FURANONES AS COX-2 INHIBITORS

[75] Inventors: Cameron Black, Point Claire; Erich Grimm, Baie D'Urfe; Zhaoyin Wang, Pierrefonds; Serge Leger, Dollard des Ormeaux, all of Canada

[73] Assignee: Merck Frosst Canada Inc., Kirkland, Canada

[21] Appl. No.: 443,620

[22] Filed: May 18, 1995

[51] Int. Cl.$^6$ .................... A61K 31/365; C07D 307/60
[52] U.S. Cl. .................... 514/473; 548/204; 548/206; 548/236; 548/333; 548/405; 549/313; 549/318
[58] Field of Search .................... 549/313, 318; 514/473

[56] References Cited

U.S. PATENT DOCUMENTS

| | | | |
|---|---|---|---|
| 4,302,461 | 11/1981 | Cherkofsky | 549/80 |
| 4,427,693 | 1/1984 | Haber | 546/256 |
| 5,207,817 | 5/1993 | Kramer et al. | 504/299 |
| 5,344,991 | 9/1994 | Reitz et al. | 568/34 |
| 5,393,790 | 2/1995 | Reitz et al. | 514/709 |

FOREIGN PATENT DOCUMENTS

| | | |
|---|---|---|
| 48 091 058 | 11/1973 | Japan . |
| 48 091 061 | 11/1973 | Japan . |
| 50 121 261 | 9/1975 | Japan . |
| WO 94/15932 | 7/1994 | WIPO . |
| WO 95/00501 | 1/1995 | WIPO . |
| WO 95/05376 | 2/1995 | WIPO . |

OTHER PUBLICATIONS

Dikshit, et al., Indian Journal of Chem., vol. 29B, pp. 954–960 (1990).

Lombardino, et al., Arzneim–Forsch. (Drug Res.), vol. 25, NR. 10, pp. 1629–1635 (1975).

Yang, et al., J. Chem. Soc., Chem. Commun., pp. 656–658 (1992).

*Primary Examiner*—Bernard Dentz
*Attorney, Agent, or Firm*—Curtis C. Panzer; David L. Rose

[57] ABSTRACT

The invention encompasses the novel compound of Formula I as well as a method of treating cyclooxygenase-2 mediated diseases comprising administration to a patient in need of such treatment of a non-toxic therapeutically effective amount of a compound of Formula I.

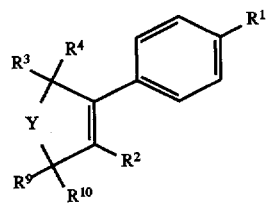

The invention also encompasses certain pharmaceutical compositions for treatment of cyclooxygenase-2 mediated diseases comprising compounds of Formula I.

18 Claims, No Drawings

5,691,374

DIARYL-5-OXYGENATED-2-(5H)-FURANONES AS COX-2 INHIBITORS

BACKGROUND OF THE INVENTION

This invention relates to methods of treating cyclooxygenase mediated diseases and certain pharmaceutical compositions therefor.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 (COX-1 ) or the constitutive enzyme, as originally identified in bovine seminal vesicles. More recently the gene for a second inducible form of cyclooxygenase, cyclooxygenase-2 (COX-2), has been cloned, sequenced and characterized initially from chicken, murine and human sources. This enzyme is distinct from the cyclooxygenase-1 which has been cloned, sequenced and characterized from various sources including the sheep, the mouse and man. The second form of cyclooxygenase, cyclooxygenase-2, is rapidly and readily inducible by a number of agents including mitogens, endotoxin, hormones, cytokines and growth factors. As prostaglandins have both physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2 (COX-2), is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

A brief description of the potential utilities of cyclooxygenase-2 inhibitors is given in an article by John Vane, *Nature*, Vol. 367, pp. 215–216, 1994 and in an article in *Drug News and Perspectives*, Vol. 7, pp. 501–512, 1994.

SUMMARY OF THE INVENTION

The invention encompasses the novel compound of Formula I as well as a method of treating cyclooxygenase-2 mediated diseases comprising administration to a patient in need of such treatment of a non-toxic therapeutically effective amount of a compound of Formula I.

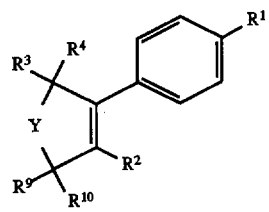

The invention also encompasses certain pharmaceutical compositions for treatment of cyclooxygenase-2 mediated diseases, comprising compounds of Formula I.

DETAILED DESCRIPTION OF THE INVENTION

The invention encompasses the novel compound of Formula I as well as a method of treating cyclooxygenase-2 mediated diseases comprising administration to a patient in need of such treatment of a non-toxic therapeutically effective amount of a compound of Formula I.

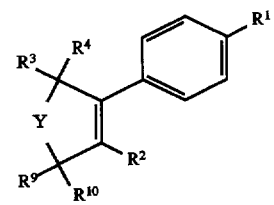

or a pharmaceutically acceptable salt thereof wherein:

Y is selected from the group consisting of
(a) $C(R^{11})(R^{12})$,
(b) oxygen,
(c) sulfur, $R^1$ is selected from the group consisting of
(a) $S(O)_2CH_3$,
(b) $S(O)_2NH_2$,
(c) $S(O)hd 2NHC(O)CF_3$,
(d) $S(O)(NH)NH_2$,
(e) $S(O)(NH)NHC(O)CF_3$,
(f) $S(O)_2NHMe$
(g) $P(O)(CH_3)NH_2$,
(h) $P(O)(CH_3)_2$,
(i) $C(S)NH_2$ $R^2$ is selected from the group consisting of
(a) $C_{1-10}$alkyl,
(b) $C_{3-10}$cycloalkyl,
(c) $C_{1-10}$alkenyl
(d) $C_{1-10}$alkynyl
(e) $C_{3-10}$cycloalkenyl
(f) mono-, di-, tri- or tetra-substituted $C_3-C_{10}$cycloalkenyl wherein the substituent is selected from the group consisting of
  (1) halo,
  (2) $C_{1-6}$alkoxy,
  (3) $C_{1-6}$alkylthio,
  (4) CN,
  (5) $CF_3$,
  (6) $C_{1-10}$alkyl,
  (7) $N_3$,
  (8) —$CO_2H$,
  (9) —$CO_2$-$C_{1-10}$alkyl,
  (10) —$C(R^5)(R^6)$-OH,

(11) —C($R^5$)($R^6$)-O-$C_{1-4}$alkyl, and
(12) —$C_{1-10}$alkyl-$CO_2$-$R^5$;
(13) benzyloxy,
(14) —O-($C_{1-10}$alkyl)-$CO_2R^5$,
(15) —O-($C_{1-10}$alkyl)-$NR^5R_6$, (g) unsubstituted or mono-, di- or tri-substituted phenyl or naphthyl wherein the substituent is selected from the group consisting of
(1) $C_{1-10}$alkyl,
(2) $C_{1-10}$alkoxy,
(3) $C_{1-10}$alkylthio,
(4) CN,
(5) $CF_3$,
(6) halo,
(7) $N_3$,
(8) —$CO_2H$,
(9) —$CO_2$-$C_{1-10}$alkyl,
(10) —C($R^5$)($R^6$)-OH,
(11) —C($R^5$)($R^6$)-O-$C_{1-4}$alkyl, and
(12) —$C_{1-6}$alkyl-$CO_2$-$R^5$;
(13) benzyloxy,
(14) —O-($C_{1-10}$alkyl)-$CO_2R^5$,
(15) —O-($C_{1-10}$alkyl)-$NR^5R^6$, (h) unsubstituted or mono-, di- or tri-substituted heteroaryl wherein the heteroaryl is a monocyclic aromatic ring of 5 atoms, said ring having one hetero atom which is S, O, or N, and optionally 1, 2, or 3 additional N atoms; or the heteroaryl is a monocyclic ring of 6 atoms, said ring having one hetero atom which is N, and optionally 1, 2, 3, or 4 additional N atoms, said substituents being selected from the group consisting of
(1) $C_{1-10}$alkyl,
(2) $C_{1-10}$alkoxy,
(3) $C_{1-10}$alkylthio,
(4) CN,
(5) $CF_3$,
(6) halo,
(7) $N_3$,
(8) —$CO_2H$,
(9) —$CO_2$-$C_{1-10}$alkyl,
(10) —C($R^5$)($R^6$)-OH,
(11) —C($R^5$)($R^6$)-O-$C_{1-4}$alkyl, and
(12) —$C_{1-6}$alkyl-$CO_2$-$R^5$;
(13) benzyloxy,
(14) —O-($C_{1-10}$alkyl)-$CO_2R^5$,
(15) —O-($C_{1-10}$alkyl)-$NR^5R^6$, (i) an unsubstituted or a mono-, di-, tri- or tetra-substituted benzoheterocycle in which the heterocycle is a 5, 6, or 7-membered ring which may contain 1 or 2 heteroatoms chosen independently from O, S, or N and which may contain a carbonyl group or a sulfonyl group; the said substituents are selected from the group consisting of
(1) $C_{1-10}$alkyl,
(2) $C_{1-10}$alkoxy,
(3) $C_{1-10}$alkylthio,
(4) CN,
(5) $CF_3$,
(6) halo,
(7) $N_3$,
(8) —$CO_2H$,
(9) —$CO_2$-$C_{1-10}$alkyl,
(10) —C($R^5$)($R^6$)-OH,
(11) —C($R^5$)($R^6$)-O-$C_{1-4}$alkyl, and
(12) —$C_{1-6}$alkyl-$CO_2$-$R^5$;
(13) benzyloxy,
(14) —O-($C_{1-10}$alkyl)-$CO_2R^5$,
(15) —O-($C_{1-10}$alkyl)-$NR^5R^6$, (j) a heterocycloalkyl group of 5, 6 or 7 members which contains 1 or 2 heteroatoms chosen from O, S, or N and optionally contains a carbonyl group or a sulfonyl group.

(k) an unsubstituted or a mono- or di- substituted benzocarbocycle in which the carbocycle is a 5, 6, or 7-membered ring which optionally contains a carbonyl group, the said substituents are selected from the group consisting of
(1) $C_{1-10}$alkyl,
(2) $C_{1-10}$alkoxy,
(3) $C_{1-10}$alkylthio,
(4) CN,
(5) $CF_3$,
(6) halo,
(7) $N_3$,
(8) —$CO_2H$,
(9) —$CO_2$-$C_{1-10}$alkyl,
(10) —C($R^5$)($R^6$)-OH,
(11) —C($R^5$)($R^6$)-O-$C_{1-4}$alkyl, and
(12) —$C_{1-6}$alkyl-$CO_2$-$R^5$;
(13) benzyloxy,
(14) —O-($C_{1-10}$alkyl)-$CO_2R^5$,
(15) —O-($C_{1-10}$alkyl)-$NR^5R^6$, $R^3$ is hydrogen, $C_{1-10}$alkyl, $CH_2OR^7$, CN, $CH_2CN$, or $C_{1-6}$fluoroalkyl, F, $CONR^7_2$, unsubstituted or mono- or di-substituted phenyl, unsubstituted or mono or di-substituted benzyl, unsubstituted or mono- or di-substituted heteroaryl, unsubstituted or mono or di-substituted heteroarylmethyl, wherein the substituents are selected from the group consisting of
(1) $C_{1-10}$alkyl,
(2) $C_{1-10}$alkoxy,
(3) $C_{1-10}$alkylthio,
(4) CN,
(5) $CF_3$,
(6) halo,
(7) $N_3$,
(8) —$CO_2H$,
(9) —$CO_2$-$C_{1-10}$alkyl,
(10) —C($R^5$)($R^6$)-OH,
(11) —C($R^5$)($R^6$)-O-$C_{1-4}$alkyl, and
(12) —$C_{1-6}$alkyl-$CO_2$-$R^5$;
(13) benzyloxy,
(14) —O-($C_{1-10}$alkyl)-$CO_2R^5$,
(15) —O-($C_{1-10}$alkyl)-$NR^5R^6$, $R^4$ is
(a) $C_{1-10}$alkoxy,
(b) $C_{1-10}$alkylthio,
(c) —OH,
(d) —$OCOR^7$,
(e) —SH,
(f) —$SCOR^7$,
(g) —$OCO_2R^8$,
(h) —$SCO_2R^8$,
(i) $OCONR^7_2$, and
(j) $SCONR^7_2$;
(k) $C_{3-10}$cycloalkoxy,
(l) $C_{3-10}$cycloalkylthio;
(m) —$NR^7_2$;

each $R^5$ or $R^6$ is independently selected from the group consisting of
(a) hydrogen, and
(b) $C_{1-10}$alkyl,
or $R^5$ and $R^6$ together with the carbon to which they are attached form a saturated monocyclic carbon ring of 3, 4, 5, 6 or 7 atoms;

each R⁷ is independently selected from the group consisting of
(a) hydrogen and
(b) R⁸;

each R⁸ is independently selected from the group consisting of
(a) $C_{1-10}$alkyl,
(b) phenyl or monosubstituted phenyl wherein the substituents may be halo, $C_{1-10}$alkyl, $C_{1-10}$alkoxy, $C_{1-10}$alkylthio, CN, or $CF_3$,
(c) benzyl or monosubstituted benzyl wherein the substituents may be halo, $C_{1-10}$alkyl, $C_{1-10}$alkoxy, $C_{1-10}$alkylthio, CN, or $CF_3$, and
(d) $C_{3-10}$cycloalkyl R⁹ and R¹⁰ are independently selected from the group consisting of:
(a) hydrogen,
(b) $C_{1-10}$alkyl,
(c) $C_{3-10}$cycloalkyl, or
R⁹ and R¹⁰ together form a double bonded O or S;

R¹¹ and R¹² are independently selected from the group consisting of:
(a) hydrogen,
(b) unsubstituted or mono- or di-substituted phenyl or unsubstituted or mono- or di-substituted benzyl or unsubstituted or mono- or di-substituted heteroaryl, or unsubstituted or mono- or di-substituted heteroarylmethyl, said substituents being selected from the group consisting of:
(1) $C_{1-10}$alkyl,
(2) $C_{1-10}$alkoxy,
(3) $C_{1-10}$alkylthio,
(4) CN,
(5) $CF_3$,
(6) halo,
(7) $N_3$,
(8) —$CO_2H$,
(9) —$CO_2$-$C_{1-10}$alkyl,
(10) —$C(R^5)(R^6)$-OH,
(11) —$C(R^5)(R^6)$-O-$C_{1-4}$alkyl, and
(12) —$C_{1-6}$alkyl-$CO_2$-R⁵;
(13) benzyloxy,
(14) —O-($C_{1-10}$alkyl )-$CO_2R^5$,
(15) —O-($C_{1-10}$alkyl)-$NR^5R^6$,
(c) $C_{1-10}$alkyl, $CH_2OR^7$, CN, $CH_2CN$, $C_{1-10}$fluoroalkyl, F or $CONR^7_2$; or
R¹¹ and R¹² together with the carbon to which they are attached form a carbonyl or a saturated monocyclic carbon ring of 3, 4, 5, 6 or 7 atoms;

R¹³ and R14 are independently selected from the group consisting of:
(a) hydrogen,
(b) $C_{1-10}$alkyl, or
R¹³ and R¹⁴ together with the carbon to which they are attached form a carbonyl, —C(=S)—, or a saturated monocyclic carbon ring of 3, 4, 5, 6, or 7 atoms.

In one genus this invention is directed to compounds of the formula

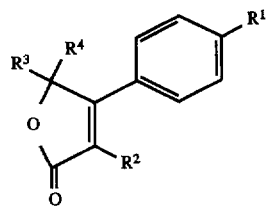

Ia wherein:

R¹ is selected from the group consisting of
(a) $S(O)_2CH_3$,
(b) $S(O)_2NH_2$,
(c) $S(O)_2NHC(O)CF_3$,
(d) $S(O)(NH)NH_2$;

R² is selected from the group consisting of unsubstituted or mono-, di- or tri-substituted phenyl wherein the substituent is selected from the group consisting of
(1) halo,
(2) $C_{1-4}$alkoxy,
(3) $C_{1-4}$alkylthio,
(4) CN,
(5) $CF_3$,
(6) $C_{1-4}$alkyl,
(7) $N_3$,
(8) —$C(R^5)(R^6)$-OH, R³ is hydrogen, $C_{1-4}$alkyl, $CH_2OR^7$, CN, $CH_2CN$, or $C_{1-4}$fluoroalkyl, F, $CONR^7_2$;

R⁴ is
(a) $C_{1-4}$alkoxy,
(b) $C_{1-4}$alkylthio,
(c) —OH,
(d) —$OCOR^7$,
(e) —SH,
(f) —$SCOR^7$,
(g) —$OCO_2R^8$,
(h) —$SCO_2R^8$,
(i) $OCONR^7_2$, and
(j) $SCONR^7_2$;

each R⁵ or R⁶ is independently selected from the group consisting of
(a) hydrogen, and
(b) $C_{1-4}$alkyl, each R⁷ is independently selected from the group consisting of
(a) hydrogen and
(b) R⁸;

each R⁸ is independently selected from the group consisting of
(a) $C_{1-4}$alkyl,
(b) phenyl or monosubstituted phenyl wherein the substituents may be halo, $C_{1-4}$alkyl, $C_{1-4}$alkoxy, $C_{1-4}$alkylthio, CN, or $CF_3$;
(c) benzyl or monosubstituted benzyl wherein the substituents may be halo, $C_{1-4}$alkyl, $C_{1-4}$alkoxy, $C_{1-4}$alkylthio, CN, or $CF_3$.

Within this this genus are the compounds of formula Ib

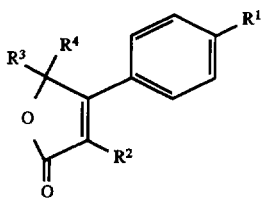

wherein:

$R^1$ is selected from the group consisting of
(a) $S(O)_2CH_3$,
(b) $S(O)_2NH_2$, $R^2$ is selected from the group consisting of unsubstituted or mono-, di- or tri-substituted phenyl wherein the substituent is selected from the group consisting of
(1) halo,
(2) $C_{1-3}$alkoxy,
(3) $CF_3$,
(4) $C_{1-3}$alkyl, $R^3$ is hydrogen, $C_{1-3}$alkyl, $CH_2OR^7$, $C_{1-4}$fluoroalkyl;
$R^4$ is
(a) $C_{1-3}$alkoxy,
(b) $C_{1-3}$alkylthio,
(c) —OH,
(d) —OCOR$^7$,
(e) —SCOR$^7$,
(f) OCONR$^7_2$, and
(g) SCONR$^7_2$;

each $R^7$ is independently selected from the group consisting of
(a) hydrogen and
(b) $R^8$;

each $R^8$ is $C_{1-3}$alkyl.

For purposes of this specification heteroaryl as in $R^2$ is intended to include, but is not limited to optionally mono- or di-substituted
(1) furanyl,
(2) diazinyl, triazinyl, tetrazinyl,
(3) imidazolyl,
(4) isooxazolyl,
(5) isothiazolyl,
(6) oxadiazolyl,
(7) oxazolyl,
(8) pyrazolyl,
(9) pyrrolyl,
(10) thiadiazolyl,
(11) thiazolyl,
(12) thienyl,
(13) triazolyl, or
(14) tetrazolyl.

Similarly, for purposes of this specification cyclic groups such as a heterocycloalkyl or benzocarbocycle or benzoheterocycle such as in $R^2$ is intended to include, but is not limited to optionally mono- or di-substituted
(1) indolyl,
(2) benzofuranyl,
(3) benzothienyl,

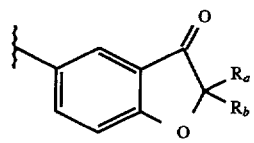 (4)

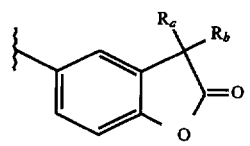 (5)

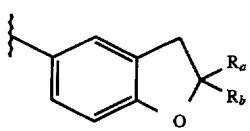 (6)

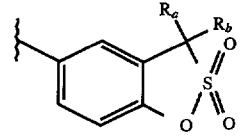 (7)

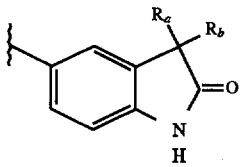 (8)

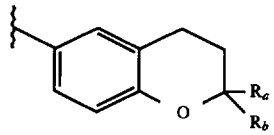 (9)

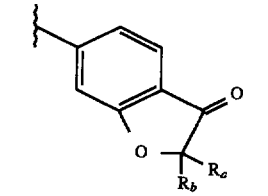 (10)

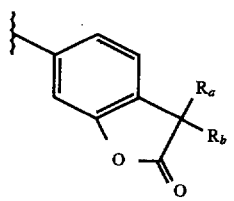 (11)

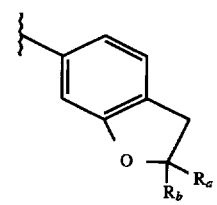 (12)

(13) 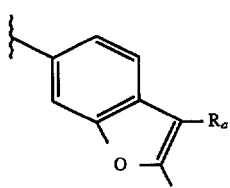

(14) 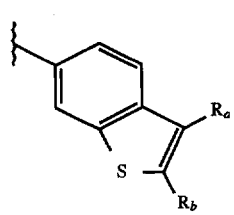

(15) 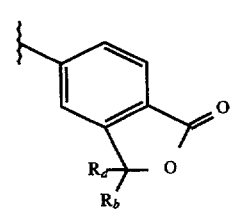

(16) 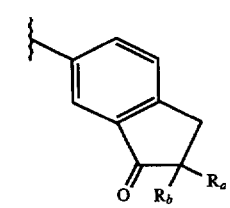

(17) 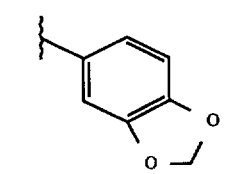

(18) 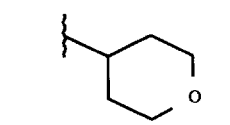

(19) 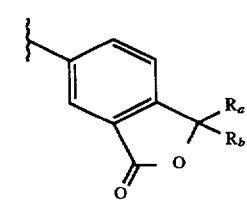

(20) 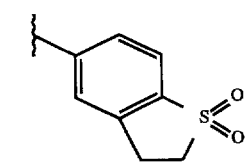

(21) 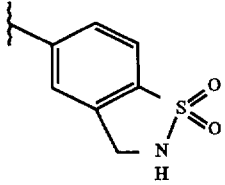

(22) 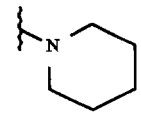

(23) 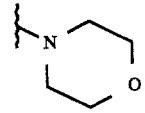

(24) 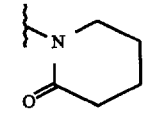

(22)

in which the substituents comprise $R_a$ and $R_b$ and said substituents are selected from halo, —OH, $CF_3$, $C_{1-3}$alkoxy, $C_{1-3}$alkylthio, and $C_{1-3}$alkyl.

One genus of compounds of formula I is that in which $R^9$ and $R^{10}$ form a double-bonded O, and Y is O.

For purposes of this specification, alkyl is defined to include linear, branched, and cyclic structures, with $C_{1-10}$alkyl including, but not restricted to, methyl, ethyl, propyl, 2-propyl, n-, i-, s- and t-butyl, pentyl, hexyl, 1,1-dimethylethyl, cyclopropyl, cyclobutyl, cyclopentyl, cyclohexyl and decyl. Similarly, $C_{1-10}$alkoxy is intended to include alkoxy groups of from 1 to 10 carbon atoms of a straight, branched, or cyclic configuration. Examples of alkoxy groups include methoxy, ethoxy, propoxy, isopropoxy, cyclopropyloxy, cyclohexyloxy, and the like. Likewise, $C_{1-10}$alkylthio is intended to include alkylthio groups of from 1 to 10 carbon atoms of a straight, branched or cyclic configuration. Examples of alkylthio groups include methylthio, n-propylthio, isopropylthio, cyclohexylthio, decylthio, etc. By way of illustration, the propylthio group signifies —$SCH_2CH_2CH_3$. $C_{1-10}$fluoroalkyl includes alkyl groups of from 1 to 10 carbon atoms of a straight, branched or cyclic configuration, in which one or more hydrogen is replaced by fluorine. Examples are —$CHF_2$, $CH_2F$, —$CF_3$, —$CH_2CF_3$, cpr-$F_5$, c-Hex-$F_{11}$, n-$C_9H_{18}CF_3$, and the like. Halo includes F, Cl, Br, or I. Heteroaryl includes furan, thiophene, pyrrole, isoxazole, isothiazole, pyrazole, oxazole, thiazole, imidazole, 1,2,3-oxadiazole, 1,2,3-thiadiazole, 1,2,3-triazole, 1,3,4-oxadiazole, 1,3,4-thiadiazole, 1,3,4-triazole, 1,2,5-oxadiazole, 1,2,5-thiadiazole, pyridine, pyridazine, pyrimidine, pyrazine, 1,2,4-triazine, 1,3,5-triazine, 1,2,4,5-tetrazine, and the like. The term aryl refers to both all-carbon (e.g. benzene, naphthalene) or heteroaryl aromatic rings.

As will be appreciated by those of skill in the art, when a substituent (e.g. alkyl, aryl, $R^1$ through $R^{14}$, etc.) occurs more than one time in a variable or in formula I, its definition at one occurance is independent of its definition at every other occurance. For example, in $CONR^7 2$, the two $R^7$'s need not be simulataneously the same, although each selection must be consistant with the markush group defining $R^7$.

Exemplifying the invention are:

(1) Benzoic acid, 3-(4-(methylsulfonyl)phenyl)-5-oxo-4-phenyl-2,5-dihydrofuran-2-yl ester, (2) 5-Hydroxy-4-(4-(methylsulfonyl)phenyl)-3-phenyl-2-(5H)-furanone, (3) 5-Hydroxy-3-(3,4-difluorophenyl)-4-(4-(methylsulfonyl)phenyl)-2-(5H)-furanone, (4) 5-Hydroxy-5-methyl-4-(4-(methylsulfonyl)phenyl)-3-phenyl-2-(5H)-furanone, (5) 3-(4-Fluorophenyl)-5-hydroxy-5-methyl-4-(4-(methylsulfonyl)phenyl)-2-(5H)-furanone,

(25) Sodium 2-(4-fluorophenyl)-3-((4-methylsulfonyl)phenyl)-4-oxo-2-pentenoate.

Some of the compounds of Formula I of the present invention in which $R^4$=OH may exist in a tautomeric open chain keto-acid form of Formula IIa or IIb below, depending on the substituents at $R^1$, $R^2$, or $R^3$ or the pH. In such cases, the rate of equilibration may vary, and activity may reside with either tautomer. In particular, it may be possible to form a salt of compound Ic with a base, said salt existing predominantly in the tautomeric form IIa.

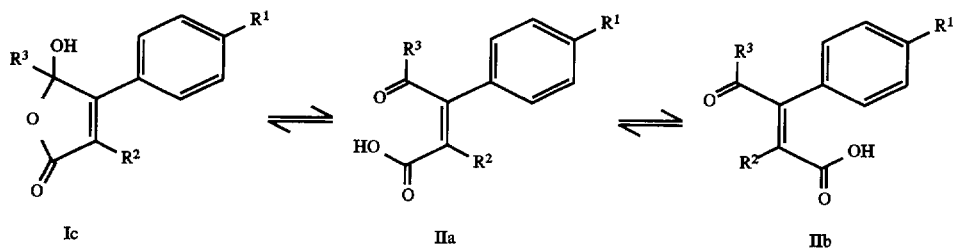

Ic        IIa        IIb (6) 3-(4-Chlorophenyl)-5-hydroxy-5-methyl-4-(4-(methylsulfonyl)phenyl)-2-(5H)-furanone, (7) 3-(3,4-Difluorophenyl)-5-hydroxy-5-methyl-4-(4-(methylsulfonyl)phenyl)-2-(5H)-furanone, (8) 3-(3-Fluorophenyl)-5-hydroxy-5-methyl-4-(4-(methylsulfonyl)phenyl)-2-(5H)-furanone, (9) 3-(3,5-Difluorophenyl)-5-hydroxy-5-methyl-4-(4-(methylsulfonyl)phenyl)-2-(5H)-furanone,

(10) 5-Methoxy-5-methyl-4-(4-(methylsulfonyl)phenyl)-3-phenyl-2-(5H)-furanone,

(11) 3-(4-Chlorophenyl)-5-methoxy-5-methyl-4-(4-(methylsulfonyl)phenyl)-2-(5H)-furanone,

(12) 3-(3,4-Difluorophenyl)-5-methoxy-5-methyl-4-(4-(methylsulfonyl)phenyl)-2-(5H)-furanone,

(13) 3-(3-Fluorophenyl)-5-methoxy-5-methyl-4-(4-(methylsulfonyl)phenyl)-2-(5H)-furanone,

(14) 3-(3,5-Difluorophenyl)-5-methoxy-5-methyl-4-(4-(methylsulfonyl)phenyl)-2-(5H)-furanone,

(15) 3-(4-Fluorophenyl)-5-methoxy-5-methyl-4-(4-(methylsulfonyl)phenyl)-2-(5H)-furanone,

(16) 5-Ethoxy-3-(4-fluorophenyl)-5-methyl-4-(4-(methylsulfonyl)phenyl)-2-(5H)-furanone,

(17) 3-(4-Fluorophenyl)-5-methyl-4-(4-(methylsulfonyl)phenyl)-5-propoxy-2-(5H)-furanone,

(18) 3-(4-Fluorophenyl)-5-isopropoxy-5-methyl-4-(4-(methylsulfonyl)phenyl)-2-(5H)-furanone,

(19) 5-Methyl-5-methylthio-4-(4-(methylsulfonyl)phenyl)-3-phenyl-2-(5H)-furanone,

(20) 5-Ethylthio-5-methyl-4-(4-(methylsulfonyl)phenyl)-3-phenyl-2-(5H)-furanone,

(21) 5-Ethyl-5-hydroxy-4-(4-(methylsulfonyl)phenyl)-3-phenyl-2-(5H)-furanone,

(22) 5-Ethyl-3-(3-fluorophenyl)-5-hydroxy-4-(4-(methylsulfonyl)phenyl)-2-(5H)-furanone,

(23) Acetic acid, 3-(4-(methylsulfonyl)phenyl)-2-methyl-5-oxo-4-phenyl-2,5-dihydrofuran-2-yl ester

(24) 5-Hydroxy-5-methyl-4-((4-methylsulfonyl)phenyl)-3-(2-naphthyl)-2-(5H)-furanone, and Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

In a second embodiment, the invention encompasses pharmaceutical compositions for inhibiting cyclooxygenase and for treating cyclooxygenase mediated diseases as disclosed herein comprising a pharmaceutically acceptable carrier and a non-toxic therapeutically effective amount of compound of formula I as described above.

Within this embodiment the invention encompasses pharmaceutical compositions for inhibiting COX-2 and for treating COX-2 mediated diseases as disclosed herein comprising a pharmaceutically acceptable carrier and a non-toxic therapeutically effective amount of compound of formula I as described above.

In a third embodiment, the invention encompasses a method of inhibiting cyclooxygenase and treating cyclooxygenase mediated diseases, advantageously treated by an active agent that selectively inhibits COX-2 in preference to COX-1 as disclosed herein comprising: administration to a patient in need of such treatment of a non-toxic therapeutically effective amount of a compound of Formula I as disclosed herein.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment which follows, references to the compounds of Formula I are meant to also include the pharmaceutically acceptable salts.

The Compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compound I may also be of use in the treatment and/or prevention of cyclooxygenase-mediated proliferative disorders such as may occur in diabetic retinopathy and tumour angiogenesis.

Compound I will also inhibit prostanoid-induced smooth muscle contraction by preventing the synthesis of contractile prostanoids and hence may be of use in the treatment of dysmenorrhea, premature labor, asthma and eosinophil related disorders. It will also be of use in the treatment of Alzheimer's disease, and for the prevention of bone loss (treatment of osteoporosis).

By virtue of its high COX-2 inhibitory activity and/or its specificity for COX-2 over COX-1, Compound I will prove useful as an alternative to conventional non-steroidal anti-inflammatory drugs (NSAID'S) particularly where such non-steroidal antiinflammatory drugs may be contraindicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

Similarly, Compound I, will be useful as a partial or complete substitute for conventional NSAID'S in preparations wherein they are presently co-administered with other agents or ingredients. Thus in further aspects, the invention encompasses pharmaceutical compositions for treating COX-2 mediated diseases as defined above comprising a non-toxic therapeutically effective amount of the compound of Formula I as defined above and one or more ingredients such as another pain reliever including acetominophen or phenacetin; a potentiator including caffeine; an $H_2$-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a diuretic; a sedating or non-sedating antihistamine. In addition the invention encompasses a method of treating cyclooxygenase mediated diseases comprising: administration to a patient in need of such treatment a non-toxic therapeutically effect amount of the compound of Formula I, optionally co-administered with one or more of such ingredients as listed immediately above.

For the treatment of any of these cyclooxygenase mediated diseases Compound I may be administered orally, topically, parenterally, by inhalation spray or rectally in dosage unit formulations containing conventional non-toxic pharmaceutically acceptable carders, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating COX-2 mediated diseases as defined may optionally include one or more ingredients as listed above.

The pharmaceutical compositions containing the active ingredient may be in a form suitable for oral Use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example, sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of an oil-in-water emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxy-ethylene sorbitan monooleate. The emulsions may also contain sweetening and flavouring agents.

Syrups and elixirs may be formulated with sweetening agents, for example, glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention can be prepared according to the following methods.

Method A

An appropriately substituted aryl bromomethyl ketone is reacted with an appropriately substituted aryl acetic acid in a solvent such as acetonitrile in the presence of a base such as triethylamine and then treated with 1,8-diazabicyclo [5.4.0]undec-7-ene (DBU) to afford lactone 1. Further treatment of 1 with DBU, followed by $(R^7COO)2$, provides ester 2, which can then be hydrolyzed with aqueous base to give hemiacetal 3.

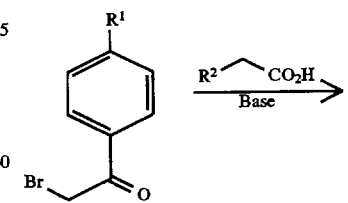

-continued

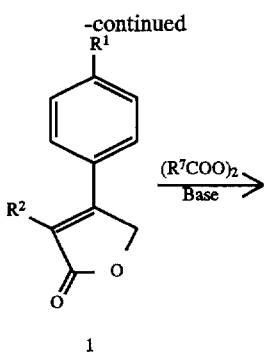

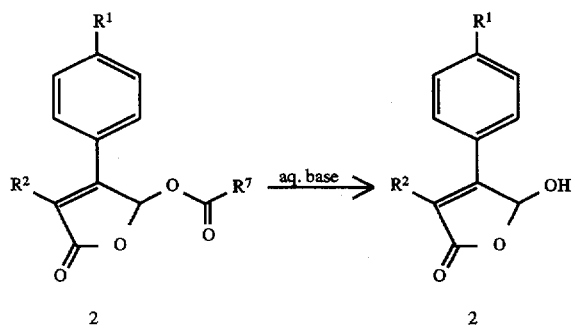

An appropriately substituted aryl bromoketone is reacted with an appropriately substituted aryl acetic acid in a solvent such as acetonitrile in the presence of a base such as triethylamine and then treated with 1,8-diazabicyclo[5.4.0]undec-7-ene (DBU) to afford lactone 4 and the crude reaction mixture can then be exposed to excess oxygen until 4 is completely oxidized to hemiketal 5.

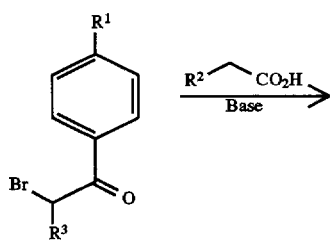

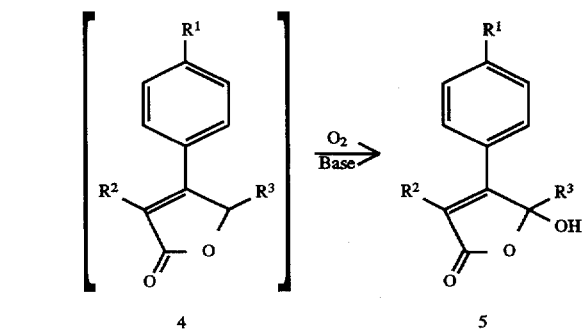

Method C

Hemiketal 5 is heated in an appropriate alcohol in the presence of a catalytic amount of acid such as $H_2SO_4$ to afford ketal 6.

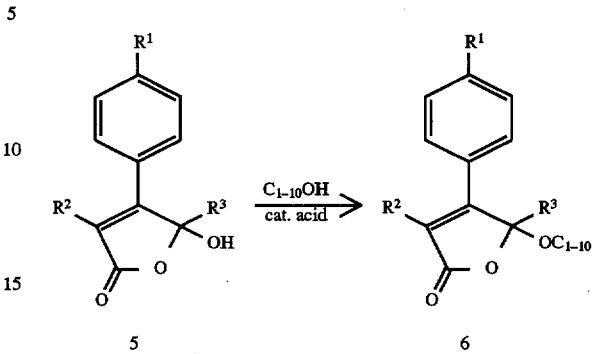

Method D

Hemiketal 5 is treated with an appropriate thiol in the presence of a Lewis acid such as $Et_2O.BF_3$ to afford thioketal 7.

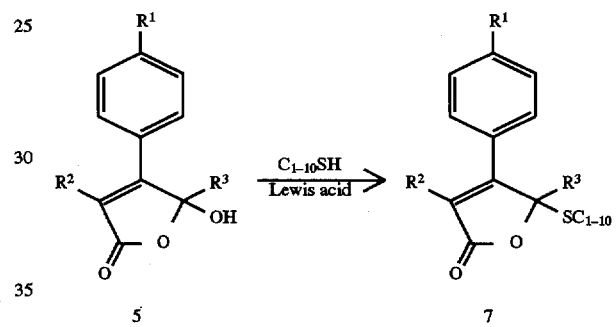

Method E

Hemiketal 5 is treated with an appropriate thio acid in the presence of a Lewis acid such as $Et_2).BF_3$ to afford thioketal 8.

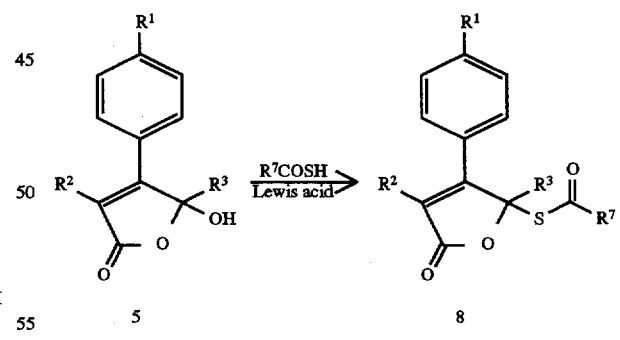

Method F

Hemiketal 5 is treated with an appropriate acid chloride or anhydride in the presence of a base to afford ketal 9

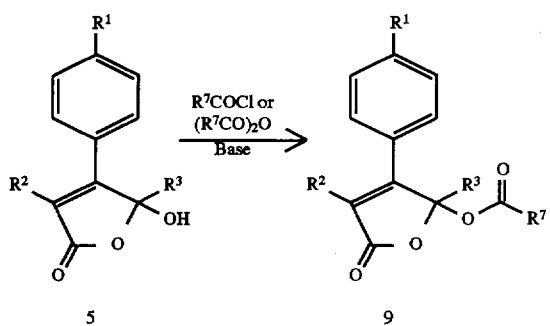
METHOD G
Hemiketal 5 is suspended in EtOH and treated with one equivalent of NaOH. The solvent is evaporated, and the salt is dissolved in water and freeze-dried to provide keto-carboxylate 10.
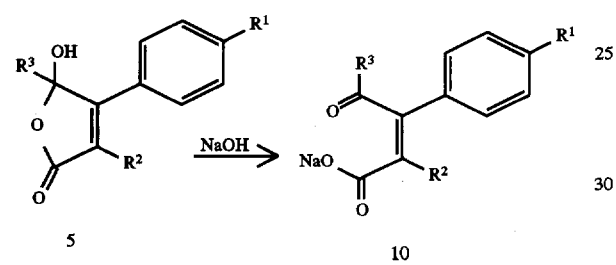
Compounds 2, 3, 5, 6, 7, 8, 9 and 10 are representives of structures of formula I.
Tables I illustrates novel compounds of the present invention.
TABLE I
| Example | Method |
|---------|--------|
| 1 | A |
| 2 | A |
| 3 | A |
| 4 | B |
| 5 | B |
| 6 | B |
| 7 | B |
| 8 | B |

TABLE I-continued

| Example | Method |
|---------|--------|
| 9 | B |
| 10 | C |
| 11 | C |
| 12 | C |
| 13 | C |
| 14 | C |
| 15 | C |
| 16 | C |
| 17 | C |
| 18 | C |
| 19 | D |
| 20 | D |

TABLE I-continued

| | Example | Method |
|---|---|---|
| (structure: phenyl, C(=O), C=C with HO-C(Et)-, 4-SO2Me-phenyl) | 21 | B |
| (structure: 3-F-phenyl, C(=O), C=C with HO-C(Et)-, 4-SO2Me-phenyl) | 22 | B |
| (structure: phenyl, C(=O), C=C with AcO-C(Me)-, 4-SO2Me-phenyl) | 23 | F |
| (structure: 2-naphthyl, C(=O), C=C with HO-C(Me)-, 4-SO2Me-phenyl) | 24 | B |
| (structure: 4-SO2Me-phenyl, C(=O), C=C with NaO-C(=O)-, 4-F-phenyl) | 25 | G |

Assays for Determining Biological Activity

The compound of Formula I can be tested using the following assays to determine their cyclooxygenase-2 inhibiting activity.

Inhibition of Cyclooxygenase Activity

Compounds were tested as inhibitors of cyclooxygenase activity in whole cell cyclooxygenase assays. Both of these assays measured prostaglandin $E_2$ synthesis in response to arachidonic acid, using a radioimmunoassay. Cells used for these assays were human osteosarcoma 143 cells (which specifically express cyclooxygenase-2) and human U-937 cells (which specifically express cyclooxygenase-1). In these assays, 100% activity is defined as the difference between prostaglandin $E_2$ synthesis in the absence and presence of arachidonate.

Assay

For cyclooxygenase assays, osteosarcoma cells are cultured in 1 mL of media in 24-well multidishes (Nunclon) until confluent (1–2×10⁵ cells/well). U-937 cells are grown in spinner flasks and resuspended to a final density of 1.5×10⁶ cells/mL in 24-well multidishes (Nunclon). Following washing and resuspension of osteosarcoma and U-937 cells in 1 mL of HBSS, 1 mL of a DMSO solution of test compound or DMSO vehicle is added, and samples gently mixed. All assays are performed in triplicate. Samples are then incubated for 5 or 15 minutes at 37° C., prior to the addition of arachidonic acid. Arachidonic acid (peroxide-free, Cayman Chemical) is prepared as a 10 mM stock solution in ethanol and further diluted 10-fold in HBSS. An aliquot of 10 mL of this diluted solution is added to the cells to give a final arachidonic acid concentration of 10 mM. Control samples are incubated with ethanol vehicle instead of arachidonic acid. Samples are again gently mixed and incubated for a further 10 min at 37° C. For osteosarcoma cells, reactions are then stopped by the addition of 100 mL of 1N HCl with mixing and by the rapid removal of the solution from cell monolayers. For U-937 cells, reactions are stopped by the addition of 100 mL of 1N HCl with mixing. Samples are then neutralized by the addition of 100 mL of 1N NaOH and $PGE_2$ levels measured by radioimmunoassay.

Rat Paw Edema Assay-Protocol

Male Sprague-Dawley rats (150–200 g) were fasted overnight and were given po either vehicle (1% methocel or 5% Tween 80) or a test compound. One hr later, a line was drawn using a permanent marker at the level above the ankle in one hind paw to define the area of the paw to be monitored. The paw volume ($V_0$) was measured using a plethysmometer (Ugo-Basile, Italy) based on the principle of water displacement. The animals were then injected subplantarly with 50 ml of 1% carrageenan solution in saline (FMC Corp, Maine) into the paw using an insulin syringe with a 25-gauge needle (i.e. 500 mg carrageenan per paw). Three hr later, the paw volume ($V_3$) was measured and the increases in paw volume ($V_3$–$V_0$) were calculated. The animals were sacrificed by $CO_2$ aphyxiation and the absence or presence of stomach lesions scored. Data were compared with the vehicle-control values and percent inhibition calculated. Since a maximum of 60–70% inhibition (paw edema) was obtained with standard NSAIDs, $ED_{50}$ values were used for comparison. All treatment groups were coded to eliminate observer bias.

NSAID-Induced Gastrophathy in Rats

Rationale

The major side effect of conventional NSAIDs is their ability to produce gastric lesions in man. This action is believed to be caused by inhibition of COX-1 in the gastrointestinal tract. Rats are particularly sensitive to the actions of NSAIDS. In fact, rat models have been used commonly in the past to evaluate the gastrointestinal side effects of current conventional NSAIDs. In the present assay, NSAID-induced gastrointestinal damage is observed by measuring fecal $^{51}Cr$ excretion after systemic injection of $^{51}Cr$-labeled red blood cells. Fecal $^{51}Cr$ excretion is a well-established and sensitive technique to detect gastrointestinal integrity in animals and man.

Methods

Male Sprague Dawley rats (150–200 g) are administered orally a test compound either once (acute dosing) or b.i.d. for 5 days (chronic dosing). Immediately after the administration of the last dose, the rats ate injected via a tail vein with 0.5 mL of $^{51}Cr$-labeled red blood cells from a donor rat. The animals are placed individually in metabolism cages with food and water ad lib. Feces are collected for a 48 h period and $^{51}$Cr fecal excretion is calculated as a percent of total injected dose.

$^{51}$Cr-labeled red blood cells are prepared using the following procedures. Ten mL of blood is collected in heparinized tubes via the vena cava from a donor rat. Plasma is removed by centrifugation and replenished with equal volume of HBSS. The red blood cells are incubated with 400 mCi of sodium $^{51}$chromate for 30 min at 37° C. At the end of the incubation, the red blood cells are washed twice with 20 mL HBSS to remove free sodium $^{51}$chromate. The red blood cells are finally reconstituted in 10 mL HBSS and 0.5 mL of the solution (about 20 mCi) is injected per rat.

Protein-Losing Gastropathy in Squirrel Monkeys
Rationale

Protein-losing gastropathy (manifested as appearance of cirulating cells and plasma proteins in the GI tract) is a significant and dose-limiting adverse response to standard NSAIDs. This can be quantitatively assessed by intravenous administration of $^{51}$CrCl$_3$ solution. This isotopic ion can avidly bind to cell and serum globins and cell endoplasmic reticulum. Measurement of radioactivity appearing in feces collected for 24 h after administration of the isotope thus provides a sensitive and quantitative index of protein-losing gastropathy.

Methods

Groups of male squirrel monkeys (0.8 to 1.4 kg) are treated by gavage with either 1% methocel or 5% Tween 80 in H$_2$O vehicles, (3 mL/kg b.i.d.) or test compounds at doses from 1–100 mg/kg b.i.d. for 5 days. Intravenous $^{51}$Cr (5 mCi/kg in 1 ml/kg PBS) is administered 1 h after the last drug/vehicle dose, and feces collected for 24 h in a metabolism cage and assessed for excreted $^{51}$Cr by gamma-counting. Venous blood is sampled 1 h and 8 h after the last drug dose, and plasma concentrations of drug measured by RP-HPLC.

Human Whole Blood (HWB) Assay
Rationale

Human whole blood provides a protein and cell-rich milieu appropriate for the study of biochemical efficacy of anti-inflammatory compounds such as selective COX-2 inhibitors. Studies have shown that normal human blood does not contain the COX-2 enzyme. This is consistent with the observation that COX-2 inhibitors have no effect on PGE$_2$ production in normal blood. These inhibitors are active only after incubation of human whole blood with LPS (lipopolysaccharide), which induces COX-2. This assay can be used to evaluate the inhibitory effect of selective COX-2 inhibitors on PGE2 production. As well, platelets in whole blood contain a large amount of the COX-1 enzyme. Immediately following blood clotting, platelets are activated through a thrombin-mediated mechanism. This reaction results in the production of thromboxane B$_2$ (TxB$_2$) via activation of COX-1. Thus, the effect of test compounds on TxB$_2$ levels levels following blood clotting can be examined and used as an index for COX-1 activity. Therefore, the degree of selectivity by the test compound can be determined by measuring the levels of PGE$_2$ after LPS induction (COX-2) and TxB$_2$ following blood clotting (COX-1) in the same assay.

METHOD

A. COX-2 (LPS-induced PGE$_2$ production)

Fresh blood was collected in heparinized tubes by venipuncture from both male and female volunteers. The subjects had no apparent inflammatory conditions and had not taken any NSAIDs for at least 7 days prior to blood collection. Plasma was immediately obtained from a 2 mL blood aliquot to use as blank (basal levels of PGE$_2$). The remaining blood was incubated with LPS (100 mg/ml final concentration, Sigma Chem, #L-2630 from E. coli; diluted in 0.1% BSA-Phosphate buffered saline) for 5 minutes at room temperature. Five hundred mL aliquots of blood were incubated with either 2 mL vehicle (DMSO) or 2 mL of a test compound at final concentrations varying from 10 nM to 30 mM for 24 hours at 37° C. At the end of the incubation, the blood was centrifuged at 12,000×g for 5 minutes to obtain plasma. A 100 mL aliquot of plasma was mixed with 400 mL of methanol for protein precipitation. The supernatant was obtained and was assayed for PGE$_2$ using a radioimmunoassay kit (Amersham, RPA#530) after conversion of PGE$_2$ to its methyl oximate derivative according to the manufacturer's procedure.

B. COX-1 (Clotting-induced TxB$_2$ production)

Fresh blood was collected into vacutainers containing no anticoagulants. Aliquots of 500 mL were immediately transferred to siliconized microcentrifuge tubes preloaded with 2 mL of either DMSO or a test compound at final concentrations varying from 10 nM to 30 mM. The tubes were vortexed and incubated at 37° C. for 1 hour to allow blood to clot. At the end of incubation, serum was obtained by centrifugation (12,000×g for 5 min.). A 100 mL aliquot of serum was mixed with 400 mL of methanol for protein precipitation. The supernatant was obtained and was assayed for TxB$_2$ using a enzyme immunoassay kit (Cayman, #51903 1 ) according to the manufacturer's instruction.

Compounds of the present invention are inhibitors of cyclooxygenase-2 and are thereby useful in the treatment of cyclooxygenase-2 mediated diseases as enumerated above. The activities of the compounds against cyclooxygenase may be seen in the representative results shown below. In the assay, inhibition is determined by measuring the amount of prostaglandin E$_2$ (PGE$_2$) synthesized in the presence of arachidonic acid, cyclooxygenase-1 or cyclooxygenase-2 and a putative inhibitor. The IC$_{50}$ values represent the concentration of putative inhibitor required to return PGE$_2$ synthesis to 50% of that obtained as compared to the uninhibited control.

The results for inhibition of PGE$_2$ production may be seen in Table II.

TABLE II

| Example | HWB Cox-2 IC$_{50}$ (µM) | HWB Cox-1 IC$_{50}$ (µM) | Rat Paw Edema ED$_{50}$ (mg/kg) |
| --- | --- | --- | --- |
| 4 | 1.27 | | 1.53 |
| 5 | 1.41 | | 1.84 |
| 6 | 2.42 | | 1.41 |
| 10 | <0.37 | | 1.94 |
| 15 | <0.37 | >30 | 2.8 |

The following abbreviations have the indicated meanings
Ac=acetyl
Bn=benzyl
DBU=diazabicyclo[5.4.0]undec-7-ene
Et$_3$N=triethylamine
HBSS=Hank's balanced salt solution
HWB=human whole blood
KHMDS=potassium hexamethyldisilazane
LDA=lithium diisopropylamide
MMPP=magnesium monoperoxyphthalate
Ms=methanesulfonyl=mesyl
MsO=methanesulfonate=mesylate
NSAID=non-steroidal anti-inflammatory drug PCC=pyridinium chlorochromate
PDC=pyridinium dichromate
Ph=phenyl
r.t.=room temperature
rac.=racemic
TFA=trifluoroacetic acid
TfO=trifluoromethanesulfonate=triflate
Th=2- or 3-thienyl
THF=tetrahydrofuran
TLC=thin layer chromatography
Ts=p-toluenesulfonyl=tosyl
TsO=p-toluenesulfonate=tosylate
Tz=1H (or 2H)-tetrazol-5-yl
$C_3H_5$=allyl
—$SO_2Me$=methyl sulfone
—$SO_2NH_2$=sulfonamide
Alkyl Group Abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl The invention will now be illustrated by the following non-limiting examples in which, unless stated otherwise:

(i) all operations were carded out at room or ambient temperature, that is, at a temperature in the range 18°–25° C.;

(ii) evaporation of solvent was carried out using a rotary evaporator under reduced pressure (600–4000 pascals: 4.5–30 mm Hg) with a bath temperature of up to 60° C.;

(iii) he course of reactions was followed by thin layer chromatography (TLC) and reaction times are given for illustration only; (iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (d) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (liter(s)), mL (milliliters), g (gram (s)), mg (milligrams(s)), mol (moles), mmol (millimoles), eq (equivalent(s)).

EXAMPLE 1

Benzoic acid 3-(4-(methylsulfonyl)phenyl)-5-oxo-4-phenyl-2,5dihydrofuran-2-yl ester Step 1: 3-(Phenyl)-4-(4-(methylsulfonyl)phenyl)-2-(5H)-furanone To a solution of phenylacetic acid (27.4 g, 201 mmol) and 2-bromo-1-(4-(methylsulfonyl)phenyl)ethanone (WO 9500501, Ex. 9 Step 1, hereby incorporated by reference) (60 g, 216 mmol, 1.075 eq.) in acetonitrile (630 mL) at 25° C. was added slowly $Et_3N$ (30.8 mL, 1.1 eq.). The mixture was stirred for 20 min. at r.t. and then cooled in an ice bath. DBU (60.1 mL, 3 eq.) was slowly added. After stirring for 20 min. in the ice bath, the reaction was complete and the mixture was acidified with 1N HCl (color changes from dark brown to yellow). Then 2.4 L of ice and water were added, stirred for a few minutes, then the precipitate was filtered and rinsed with water (giving 64 g of crude wet product). The solid was dissolved in 750 mL of $CH_2Cl_2$ (dried over $MgSO_4$, filtered) and 300 g of silica gel was added. The solvent was evaporated to near dryness (silica gel a bit sticky) and the residue was applied on top of a silica gel plug (sintered glass funnel) and eluted with 10% $EtOAc/CH_2Cl_2$, giving after evaporation of the solvent and a swish in EtOAc, 36.6 g (58%) of the title compound.

Analysis calculated for $C_{17}H_{14}O_4S$ C, 64.95; H, 4.49; S, 10.20 Found: C, 64.63; H, 4.65; S, 10.44

Step 2: Benzoic acid 3-(4-(methylsulfonyl)phenyl)-5-oxo-4-phenyl-2,5-dihydrofuran-2-yl ester A mixture of 0.16 g of the product from Step 1, 0.18 mL of DBU and 0.31g of benzoylperoxide in 2 mL of $CH_2Cl_2$ was stirred for 3.5 h at r.t.. The reaction mixture was then diluted with 50 mL of EtOAc and washed with 50 mL of 20% $NH_4OAc$ solution. The organic layer was dried over $MgSO_4$, filtered and concentrated. The residue was purified by silica gel flash chromatography, eluting with 45% EtOAc/ hexane to give 92 mg of the title compound as a white solid.

$^1$H NMR ($d_6$-acetone, 400 MHz) δ 7.95–8.08 (5H, m), 7.85 (1H, s), 7.79 (2H, d), 7.60–7.72 (2H, m), 7.41–7.55 (6H, m), 3.14 (3H, s).

EXAMPLE 2

5-Hydroxy-4-(4-(methylsulfonyl)phenyl)-3-phenyl-2-(5H)-furanone

To a solution of 80 mg of the product from Step 2 in example 1 in 4 mL THF and 2 mL MeOH was added 0.5 mL of 2N aqueous NaOH solution. After stirring for 1 h at r.t., the reaction mixture was treated with 5 mL of 20% aqueous $NH_4OAc$ solution and extracted with 20 mL of EtOAc. The EtOAc layer was dried over $MgSO_4$, filtered and concentrated. The residue was purified by silica gel flash chromatography, eluting with 55% EtOAc/hexane to provide 10 mg of the title compound as a white solid.

$^1$H NMR ($d_6$-acetone, 400 MHz) δ 7.98 (2H, d), 7.75 (2H, d), 7.40 (5H, m), 7.00 (1H, s), 6.76 (1H, s), 3.18 (3H, s).

EXAMPLE 3

5-Hydroxy-3-(3,4-difluorophenyl)-4-(4-(methylsulfonyl)phenyl)-2-(5H)-furanone $^1$H NMR ($d_6$-acetone, 400 MHz) δ 8.01 (2H, d), 7.76 (2H, d), 7.34–7.48 (2H, m), 7.20–7.28 (1H, m), 7.10 (1H, s), 6.76 (1H, s), 3.17 (3H, s).

EXAMPLE 4

5-Hydroxy-5-methyl-4-(4-(methylsulfonyl)phenyl)-3-phenyl-2-(5H)-furanone

A mixture of 2-bromo-1-(4-methylsulfonylphenyl)-propan-1-one (prepared using the methodology of WO 9500501, Ex. 9 Step 1) (8.7 g) and phenyl acetic acid (5 g) in 150 mL of $CH_3CN$ was treated with 8.5 mL of $Et_3N$. The reaction mixture was stirred overnight at r.t. and then 12 mL of DBU was added dropwise over 2 min. After stirring for 1 h at r.t. $O_2$ was bulbed into the mixture until it became colorless (in 45 min.). The reaction mixture was then poured into a solution of 80 mL 1N HCl and 100 mL of brine, and extracted with 500 mL of 1:1 EtOAc/hexane. The extract was dried over $MgSO_4$, filtered and concentrated. The crude product was swished from 1:4 EtOAc/hexane (200 mL) to give 7.2 g of the title product as a white solid.

$^1$H NMR ($d_6$-acetone, 400 MHz) δ 7.98 (2H, d), 7.76 (2H, d), 7.32 (5H, m), 6.86 (1H, s), 3.18 (3H, s), 1.70 (3H, s).

EXAMPLE 5

3-(4-Fluorophenyl)-5-hydroxy-5-methyl-4-(4-(methylsulfonyl)phenyl)-2-(5H)-furanone $^1$H NMR ($d_6$-acetone, 300 MHz) d 7.98 (2H, d), 7.78 (2H, d), 7.42 (2H, dd), 7.12 (2H, t), 6.86 (1H, s), 3.16 (3H, s), 1.66 (3H, s).

EXAMPLE 6

3-(4-Chlorophenyl)-5-hydroxy-5-methyl-4-(4-(methylsulfonyl)phenyl)-2-(5H)-furanone $^1$H NMR ($d_6$-acetone, 400 MHz) δ 8.00 (2H, d), 7.78 (2H, d), 7.38 (3H, s), 6.90 (1H, s), 3.16 (3H, s), 1.67 (3H, s).

EXAMPLE 7

3-(3,4-Difluorophenyl)-5-hydroxy-5-methyl-4-(4-(methylsulfonyl)phenyl)-2-(5H)-furanone $^1$H NMR ($d_6$-acetone, 300 MHz) δ 8.02 (2H, d), 7.82 (2H, d), 7.25–7.42 (2H, m), 7.,15 (1H, m), 6.92 (1H, s), 3.16 (3H, s), 1.68 (3H, s).

EXAMPLE 8

3-(3-Fluorophenyl)-5-hydroxy-5-methyl-4-(4-(methylsulfonyl)phenyl)-2-(5H)-furanone $^1$H NMR ($d_6$-acetone, 300 MHz) δ 8.00 (2H, d), 7.80 (2H, d), 7.30–7.42 (1H, m), 7.10–7.22 (3H, m), 6.92 (1H, s), 3.16 (3H, s), 1.70 (3H, s).

EXAMPLE 9

3-(3,5-Difluorophenyl)-5-hydroxy-5-methyl-4-(4-(methylsulfonyl)phenyl)-2-(5H)-furanone $^1$H NMR ($d_6$-acetone, 400 MHz) δ 8.04 (2H, d), 7.82 (2H, d), 6.95–7.10 (3H, m), 6.94 (1H, s), 3.18 (3H, s), 1.70 (3H, s).

EXAMPLE 10

5-Methoxy-5-methyl-4-(4-(methylsulfonyl)phenyl)-3-phenyl-2-(5H)-furanone

To a solution of 5-hydroxy-5-methyl-4-(4-(methylsulfonyl)phenyl)-3-phenyl-2-(5H)-furanone (Example 4) (1.0 g) in 120 mL of MeOH was added 0.1 mL of concentrated $H_2SO_4$. The mixture was heated to reflux for 3 days and then treated with 2 mL of $Et_3N$. Methanol was removed under reduced pressure and the residue was purified by silica gel flash chromatography eluted with 4:1 toluene/EtOAc. After a swish from 2:1 hexane/EtOAc, 0.8 g of the title compound was obtained as a white solid.

$^1$H NMR ($d_6$-acetone, 300 MHz) δ 7.98 (2H, d), 7.70 (2H, d), 7.35–7.65 (5H, m), 3.45 (3H, s), 3.15 (3H, s), 1.66 (3H, s).

EXAMPLE 11

3-(4-Chlorophenyl)-5-methoxy-5-methyl-4-(4-(methylsulfonyl)phenyl)-2-(5H)-furanone $^1$H NMR ($d_6$-acetone, 400 MHz) δ 7.98 (2H, d), 7.70 (2H, d), 7.36–7.46 (4H, m), 3.47 (3H, s), 3.16 (3H, s), 1.68 (3H, s).

EXAMPLE 12

3-(3,4-Difluorophenyl)-5-methoxy-5-methyl-4-(4-1methylsulfonyl)phenyl)-2-(5H)-furanone $^1$H NMR ($d_6$-acetone, 300 MHz) δ 8.00 (2H, d), 7.74 (2H, d), 7.40–7.50 (1H, m), 7.28–7.40 (1H, m), 7.21–7.29 (1H, m), 3.47 (3H, s), 3.18 (3H, s), 1.65 (3H, s).

EXAMPLE 13

3-(3-Fluorophenyl)-5-methoxy-5-methyl-4-(4-(methylsulfonyl)phenyl)-2-(5H)-furanone $^1$H NMR ($d_6$-acetone, 300 MHz) δ 7.98 (2H, d), 7.71 (2H, d), 7.38–7.45 (1H, m), 7.25–7.29 (3H,m), 3.49 (3H, s), 3.16 (3H, s), 1.68 (3H, s).

EXAMPLE 14

3-(3,5-Difluorophenyl)-5-methoxy-5-methyl-4-(4-(methylsulfonyl)phenyl)-2-(5H)-furanone $^1$H NMR ($d_6$-acetone, 300 MHz) δ 8.01 (2H, d), 7.23 (2H, d), 7.05–7.14 (3H, m), 3.48 (3H, s), 3.16 (3H, s), 1.66 (3H, s).

EXAMPLE 15

3-(4-Fluorophenyl)-5-methoxy-5-methyl-4-(4-(methylsulfonyl)phenyl)-2-(5H)-furanone $^1$H NMR ($d_6$-acetone, 300 MHz) δ 8.00 (2H, d), 7.72 (2H, d), 7.44–7.52 (2H, m), 7.12–7.20 (2H, m), 3.48 (3H, s), 3.17 (3H, s), 1.66 (3H, s).

EXAMPLE 16

5-Ethoxy-3-(4-fluorophenyl)-5-methyl-4-(4-(methylsulfonyl)phenyl)-2-(5H)-furanone $^1$H NMR ($d_6$-acetone, 300 MHz) δ 7.99 (2H, d), 7.72 (2H, d), 7.44–7.53 (2H, m), 7.12–7.20 (2H, m), 3.68–3.78 (2H, m), 3.16 (3H, s), 1.67 (3H, s), 1.28 (3H, t).

EXAMPLE 17

3-(4-Fluorophenyl)-5-methyl-4-(4-(methylsulfonyl)phenyl)-5-propoxy-2-(5H)-furanone $^1$H NMR ($d_6$-acetone, 300 MHz) δ 7.96 (2H, d), 7.70 (2H, d), 7.42–7.51 (2H, m), 7.10–7.20 (2H, m), 3.62 (2H, t), 3.16 (3H, s), 1.62–1.76 (2H, m), 1.66 (3H, s), 1.00 (3H, t).

EXAMPLE 18

3-(4-Fluorophenyl)-5-isopropoxy-5-methyl-4-(4-(methylsulfonyl)phenyl)-2-(5H)-furanone $^1$H NMR (d$_6$-acetone, 300 MHz) δ 7.98 (2H, d), 7.79 (2H, d), 7.40–7.51 (2H, m), 7.11–7.19 (2H, m), 4.12–4.23 (1H, m), 3.15 (3H, s), 1.70 (3H, s), 1.26 (3H, d), 1.21 (3H, d).

EXAMPLE 19

5-Methyl-5-methylthio-4-(4-(methylsulfonyl)phenyl)-3-phenyl-2-(5H)-furanone $^1$H NMR (d$_6$-acetone, 400 MHz) δ 8.00 (2H, d), 7.81 (2H, d), 7.26–7.40 (5H, m), 3.16 (3H, s), 2.14 (3H, s), 1.80 (3H, s).

EXAMPLE 20

5-Ethylthio-5-methyl-4-(4-(methylsulfonyl)phenyl)-3-phenyl-2-(5H)-furanone $^1$H NMR (d$_6$-acetone, 300 MHz) δ 8.00 (2H, d), 7.73 (2H, d), 7.28–7.42 (5H, m), 3.16 (3H, s), 2.56–2.35 (2H, m), 1.78 (3H, s), 1.28 (3H, t).

EXAMPLE 21

5-Ethyl-5-hydroxy-4-(4-(methylsulfonyl)phenyl)-3-phenyl-2-(5H)-furanone $^1$H NMR (d$_6$-acetone, 300 MHz) δ 7.96 (2H, d), 7.80 (2H, d), 7.30–7.40 (5H, m), 6.85 (1H, s), 3.15 (3H, s), 2.0–2.15 (1H, m), 1.8–1.92 (1H, m), 0.89 (3H, t).

EXAMPLE 22

5-Ethyl-3-(3-fluorophenyl)-5-hydroxy-4-(4-(methylsulfonyl)phenyl)-2-(5H)-furanone $^1$H NMR (d$_6$-acetone, 300 MHz) δ 8.00 (2H, d), 7.80 (2H, d), 7.34–7.44 (1H, m), 7.12–7.19 (3H, m), 6.88 (1H, s), 3.15 (3H, s), 2.0–2.15 (1H, m), 1.8–1.92 (1H, m), 0.89 (3H, t).

EXAMPLE 23

Acetic acid, 3-(4-(methylsulfonyl)phenyl)-2-methyl-5-oxo-4-phenyl-2,5-dihydrofuran-2-yl ester $^1$H NMR (d$_6$-acetone, 300 MHz) δ 8.00 (2H, d), 7.65 (2H, d), 7.40–7.52 (5H, m), 3.15 (3H, s), 2.15 (3H, s), 1.83 (3H, s)

EXAMPLE 24

5-Hydroxy-5-methyl-4-((4-methylsulfonyl)phenyl)-3-(2-naphthyl)-2-(5H)-furanone $^1$H NMR (d$_6$-acetone, 300 MHz) δ 8.08 (1H, s), 7.97 (2H, m), 7.85 (6H, m), 7.52 (2H, m), 7.30 (1H, dd), 3.14 (3H, s), 1.72 (3H, s).

EXAMPLE 25

Sodium 2-(4-fluorophenyl)-3-((4-methylsulfonyl)phenyl)-4-oxo-2-pentenoate

To a solution of 3-(4-fluorophenyl)-5-hydroxy-5-methyl-4-((4-methylsulfonyl)phenyl)-2-(5H)-furanone (Example 5) (210 mg) in 4 mL of absolute ethanol was added 0.58 mL of a 1.00M sodium hydroxide solution. The resulting solution was concentrated to give a solid, which was subsequently dissolved in 4 mL of water. Lyophilization provided 210 mg of the title compound as a light orange solid.

$^1$H NMR (d$_6$-DMSO, 300 MHz) δ 7.68 (2H, m), 7.18 (2H, m), 7.03 (2H, m), 6.91 (2H, d), 3.13 (3H, s), 2.35 (3H, s).

What is claimed is:

1. A compound of formula Ib

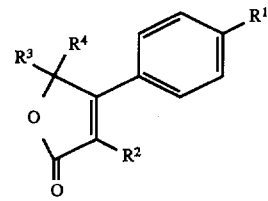

or a pharmaceutically acceptable salt thereof
wherein:

$R^1$ is selected from the group consisting of
(a) $S(O)_2CH_3$,
(b) $S(O)_2NH_2$,
(c) $S(O)_2NHC(O)CF_3$,
(d) $S(O)(NH)NH_2$,
(e) $S(O)(NH)NHC(O)CF_3$, $R^2$ is selected from the group consisting of
(a) $C_{3-6}$cycloalkyl,
(b) mono- or di- substituted $C_3$–$C_6$cycloalkenyl wherein the substituent is selected from the group consisting of
  (1) halo,
  (2) $C_{1-4}$alkoxy,
  (3) $C_{1-4}$alkylthio,
  (4) CN,
  (5) $CF_3$,
  (6) $C_{1-6}$alkyl,
  (7) $N_3$,
  (8) —$CO_2H$,
  (9) —$CO_2$-$C_{1-6}$alkyl,
  (10) —$C(R^5)(R^6)$-OH,
  (11) —$C(R^5)(R^6)$-O-$C_{1-4}$alkyl,
(c) unsubstituted or mono-, di- or tri-substituted phenyl or naphthyl wherein the substituent is selected from the group consisting of
  (1) halo,
  (2) $C_{1-4}$alkoxy,
  (3) $C_{1-4}$alkylthio,
  (4) CN,
  (5) $CF_3$,
  (6) $C_{1-6}$alkyl,
  (7) $N_3$,
  (8) —$CO_2H$,
  (9) —$CO_2$-$C_{1-4}$alkyl,
  (10) —$C(R^5)(R^6)$-OH,
  (11) —$C(R^5)(R^6)$-O-$C_{1-4}$alkyl, and
  (12) —$C_{1-4}$alkyl-$CO_2$-$R^5$;
  (13) —O—($C_{1-4}$alkyl)-$CO_2R^5$,
(d) unsubstituted or mono-, di- or tri-substituted heteroaryl wherein the heteroaryl is a monocyclic aromatic ring of 5 atoms, said ring having one hetero atom which is S, O, or N, and optionally 1, 2, or 3 additional N atoms; or
the heteroaryl is a monocyclic ring of 6 atoms, said ring having one hetero atom which is N, and optionally 1, 2 or 3 additional N atoms, said substituents are selected from the group consisting of
  (1) halo,
  (2) $C_{1-4}$alkyl,

33

(3) $C_{1-4}$alkoxy,
(4) $C_{1-4}$alkylthio,
(5) CN,
(6) $CF_3$,
(7) $N_3$,
(8) —$C(R^5)(R^6)$-OH, and
(9) —$C(R^5)(R^6)$-O-$C_{1-4}$alkyl;

(e) an unsubstituted or a mono- or di-substituted benzoheterocycle in which the heterocycle is a 5, 6, or 7-membered ring which may contain 1 or 2 heteroatoms chosen independently from O, S, or N and which may contain a carbonyl group or a sulfonyl group; the said substituents are selected from the group consisting of
(1) halo,
(2) $C_{1-4}$alkyl,
(3) $C_{1-4}$alkoxy,
(4) $C_{1-4}$alkylthio,
(5) CN,
(6) $CF_3$,
(7) $N_3$,
(8) —$C(R^5)(R^6)$-OH, and
(9) —$C(R^5)(R^6)$-O-$C_{1-4}$alkyl;

(f) a heterocycloalkyl group of 5, 6 or 7 members which contains 1 or 2 heteroatoms chosen from O, S, or N and optionally contains a carbonyl group or a sulfonyl group (g) an unsubstituted or a mono- or di-substituted benzocarbocycle in which the carbocycle is a 5, 6, or 7-membered ring which optionally contains a carbonyl group, the said substituents are selected from the group consisting of
(1) halo,
(2) $C_{1-4}$alkyl,
(3) $C_{1-4}$alkoxy,
(4) $C_{1-4}$alkylthio,
(5) CN,
(6) $CF_3$,
(7) $N_3$,
(8) —$C(R^5)(R^6)$-OH, and
(9) —$C(R^5)(R^6)$-O-$C_{1-4}$alkyl;

$R^3$ is hydrogen, $C_{1-4}$alkyl, $CH_2OR^7$, CN, $CH_2CN$, or $C_{1-4}$fluoroalkyl, F, $CONR^7_2$, unsubstituted or mono- or di-substituted phenyl, unsubstituted or mono or di-substituted benzyl, unsubstituted or mono- or di-substituted heteroaryl, unsubstituted or mono or di-substituted heteroarylmethyl, wherein the substituents are selected from the group consisting of
(1) halo,
(2) $C_{1-4}$alkyl,
(3) $C_{1-4}$alkoxy,
(4) $C_{1-4}$alkylthio,
(5) CN,
(6) $CF_3$,
(7) $N_3$,
(8)—$C(R^5)(R^6)$-OH, and
(9) —$C(R^5)(R^6)$-O-$C_{1-4}$alkyl;

$R^4$ is
(a) $C_{1-4}$alkoxy,
(b) $C_{1-4}$alkylthio,
(c) —OH,
(d) —$OCOR^7$,
(e) —SH,
(f) —$SCOR^7$,
(g) —$OCO_2R^8$,
(h) —$SCO_2R^8$,
(i) $OCONR^7_2$, and

34

(j) $SCONR^7_2$;

each $R^5$ or $R^6$ is independently selected from the group consisting of
(a) hydrogen, and
(b) $C_{1-4}$alkyl, each $R^7$ is independently selected from the group consisting of
(a) hydrogen and
(b) $R^8$;

each $R^8$ is independently selected from the group consisting of
(a) $C_{1-6}$alkyl,
(b) phenyl or monosubstituted phenyl wherein the substituents may be halo, $C_{1-4}$alkyl, $C_{1-4}$alkoxy, $C_{1-4}$alkylthio, CN, or $CF_3$,
(c) benzyl or monosubstituted benzyl wherein the substituents may be halo, $C_{1-4}$alkyl, $C_{1-4}$alkoxy, $C_{1-4}$alkylthio, CN, or $CF_3$.

2. A compound according to claim 1 wherein:
$R^1$ is selected from the group consisting of
(a) $S(O)_2CH_3$,
(b) $S(O)_2NH_2$,
(c) $S(O)$hd 2$NHC(O)CF_3$,
(d) $S(O)(NH)NH_2$,
(e) $S(O)(NH)NHC(O)CF_3$, $R^2$ is selected from the group consisting of
(a) $C_{3-6}$cycloalkyl,
(b) unsubstituted or mono-, di- or tri-substituted phenyl or naphthyl wherein the substituent is selected from the group consisting of
(1) halo,
(2) $C_{1-4}$alkoxy,
(3) $C_{1-4}$alkylthio,
(4) CN,
(5) $CF_3$,
(6) $C_{1-4}$alkyl,
(7) $N_3$,
(8) —$CO_2H$,
(9) —$CO_2$-$C_{1-4}$alkyl,
(10) —$C(R^5)(R^6)$-OH,
(11) —$C(R^5)(R^6)$-O-$C_{1-4}$alkyl, and
(12) —$C_{1-4}$alkyl-$CO_2$-$R^5$:
(13) —O-($C_{1-4}$alkyl)-$CO_2R^5$;

$R^3$ is hydrogen, $C_{1-4}$alkyl, $CH_2OR^7$, CN, $CH_2CN$, or $C_{1-4}$fluoroalkyl, F, $CONR^7_2$, unsubstituted or mono- or di-substituted phenyl, unsubstituted or mono or di-substituted benzyl, wherein the substituents are selected from the group consisting of
(1) halo,
(2) $C_{1-4}$alkyl,
(3) $C_{1-4}$alkoxy,
(4) $C_{1-4}$alkylthio,
(5) CN,
(6) $CF_3$,
(7) $N_3$,
(8)—$C(R^5)(R^6)$-OH, and
(9) —$C(R^5)(R^6$-O-$C_{1-4}$alkyl;

$R^4$ is
(a) $C_{1-4}$alkoxy,
(b) $C_{1-4}$alkylthio,
(c) —OH,
(d) —$OCOR^7$,
(e)—SH,
(f) —$SCOR^7$,
(g) —$OCO_2R^8$,
(h) —$SCO_2R^8$, (i) OCONR⁷₂, and
(j) SCONR⁷₂;

each R⁵ or R⁶ is independently selected from the group consisting of
(a) hydrogen, and
(b) $C_{1-4}$alkyl, each R⁷ is independently selected from the group consisting of
(a) hydrogen and
(b) R⁸;

each R⁸ is independently selected from the group consisting of
(a) $C_{1-4}$alkyl,
(b) phenyl or monosubstituted phenyl wherein the substituents may be halo, $C_{1-4}$alkyl, $C_{1-4}$alkoxy, $C_{1-4}$alkylthio, CN, or $CF_3$,
(c) benzyl or monosubstituted benzyl wherein the substituents may be halo, $C_{1-4}$alkyl, $C_{1-4}$alkoxy, $C_{1-4}$alkylthio, CN, or $CF_3$.

3. A compound according to claim 2 wherein:
R¹ is selected from the group consisting of
(a) $S(O)_2CH_3$,
(b) $S(O)_2NH_2$,
(c) $S(O)_2NHC(O)CF_3$,
(d) $S(O)(NH)NH_2$,
(e) $S(O)(NH)NHC(O)CF_3$;

R² is selected from the group consisting of unsubstituted or mono-, di- or tri-substituted phenyl wherein the substituent is selected from the group consisting of
(1) halo,
(2) $C_{1-4}$alkoxy,
(3) $C_{1-4}$alkylthio,
(4) CN,
(5) $CF_3$,
(6) $C_{1-4}$alkyl,
(7) $N_3$,
(8) —$CO_2H$,
(9) —$CO_2$-$C_{1-4}$alkyl,
(10) —$C(R^5)(R^6)$-OH,
(11) —$C(R^5)(R^6)$-O-$C_{1-4}$alkyl;

R³ is hydrogen, $C_{1-4}$alkyl, $CH_2OR^7$, CN, $CH_2CN$, or $C_{1-4}$fluoroalkyl, F, CONR⁷₂, unsubstituted or mono- or di-substituted phenyl, wherein the substituents are selected from the group consisting of
(1) halo,
(2) $C_{1-4}$alkyl,
(3) $C_{1-4}$alkoxy,
(4) $C_{1-4}$alkylthio,
(5) $CF_3$,
(6) $N_3$,
(7) —$C(R^5)(R^6)$-OH, and R⁴ is
(a) $C_{1-4}$alkoxy,
(b) $C_{1-4}$alkylthio,
(c) —OH,
(d) —OCOR⁷,
(e) —SH,
(f) —SCOR⁷,
(g) —$OCO_2R^8$,
(h) —$SCO_2R^8$,
(i) OCONR⁷₂, and
(j) SCONR⁷₂;

each R⁵ or R⁶ is independently selected from the group consisting of
(a) hydrogen, and
(b) $C_{1-4}$alkyl, each R⁷ is independently selected from the group consisting of
(a) hydrogen and
(b) R⁸;

each R⁸ is independently selected from the group consisting of
(a) $C_{1-4}$alkyl,
() phenyl or monosubstituted phenyl wherein the substituents may be halo, $C_{1-4}$alkyl, $C_{1-4}$alkoxy, $C_{1-4}$alkylthio, CN, or $CF_3$.

4. A compound according to claim 1 wherein:
R¹ is selected from the group consisting of
(a) $S(O)_2CH_3$,
(b) $S(O)_2NH_2$,
(c) $S(O)_2NHC(O)CF_3$,
(d) $S(O)(NH)NH_2$,
(e) $S(O)(NH)NHC(O)CF_3$, R² is selected from the group consisting of
(a) mono- or di-substituted heteroaryl selected from the group consisting of
(1) furanyl,
(2) diazinyl, triazinyl and tetrazinyl,
(3) imidazolyl,
(4) isooxazolyl,
(5) isothiazolyl,
(6) oxadiazolyl,
(7) oxazolyl,
(8) pyrazolyl,
(9) pyrrolyl,
(10) thiadiazolyl,
(11) thiazolyl,
(12) thienyl,
(13) triazolyl, and
(14) tetrazolyl, wherein said substituents are selected from the group consisting of
(1) hydrogen,
(2) fluoro, chloro, bromo and iodo,
(3) $C_{1-6}$alkyl,
(4) $C_{1-6}$alkoxy,
(5) $C_{1-6}$alkylthio,
(6) CN,
(7) $CF_3$,
(8) $N_3$,
(9) —$C(R^5)(R^6)$-OH, and
(10) —$C(R^5)(R^6)$-O-$C_{1-4}$alkyl;

(b) a mono- or di-substituted benzoheterocycle, benzocarbocycle or heterocycloalkyl selected from the group consisting of
(1) 2-indolyl,
(2) 3-indolyl,
(3) 1-methyl-5-indolyl
(4) 2-benzofuranyl,
(5) 3-benzofuranyl,
(6) 5-benzofuranyl,
(7) 6-benzofuranyl,
(8) 2-benzothienyl,
(9) 3-benzothienyl,
(10) 5-benzothienyl,
(11) 6-benzothienyl,

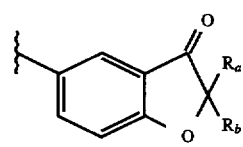 (4)

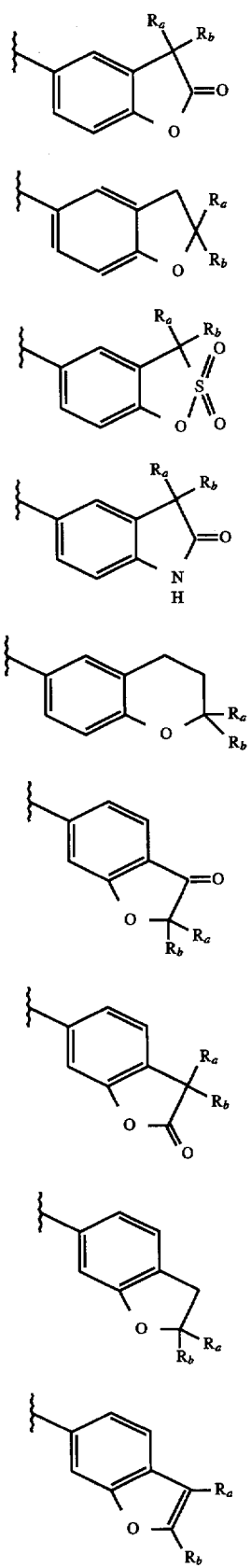
(5)
(6)
(7)
(8)
(9)
(10)
(11)
(12)
(13)
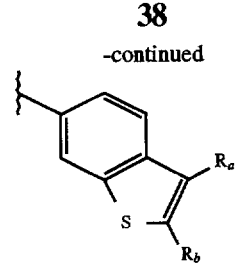
(14)
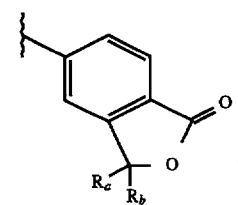
(15)
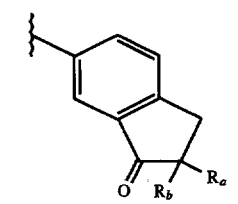
(16)
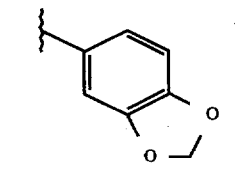
(17)
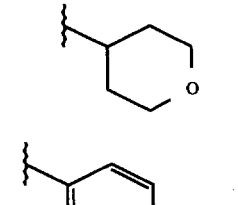
(18)
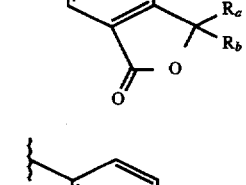
(19)
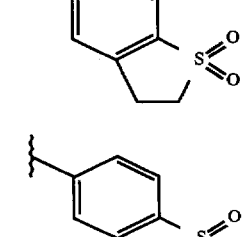
(20)
(21)
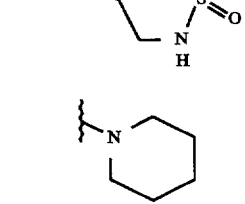
(22)

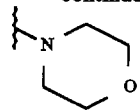
(23)

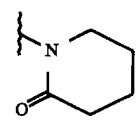
(24)

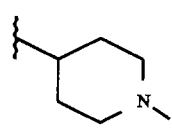
(25)

which the substituents comprise $R_a$ and $R_b$ and said substituents are selected from halo, —OH, $CF_3$, $C_{1-3}$alkoxy, $C_{1-3}$alkylthio, and $C_{1-3}$alkyl;

$R^3$ is hydrogen, $C_{1-6}$alkyl, $CH_2OR^7$, CN, $CH_2CN$, or $C_{1-6}$fluoroalkyl, F, $CONR^7{}_2$, unsubstituted or mono- or di-substituted phenyl, unsubstituted or mono or di-substituted benzyl, unsubstituted or mono- or di-substituted heteroaryl, unsubstituted or mono or di-substituted heteroarylmethyl, wherein the substituents are selected from the group consisting of
(1) halo,
(2) $C_{1-4}$alkyl,
(3) $C_{1-4}$alkoxy,
(4) $C_{1-4}$alkylthio,
(5) CN,
(6) $CF_3$,
(7) $N_3$,
(8) —$C(R^5)(R^6)$-OH, and
(9) —$C(R^5)(R^6)$-O-$C_{1-10}$alkyl;

$R^4$ is
(a) $C_{1-4}$alkoxy,
(b) $C_{1-4}$alkylthio,
(c) —OH,
(d) —$OCOR^7$,
(e) —SH,
(f) —$SCOR^7$,
(g) —$OCO_2R^8$,
(h) —$SCO_2R^8$,
(i) $OCONR^7{}_2$, and
(j) $SCONR^7{}_2$;

each $R^5$ or $R^6$ is independently selected from the group consisting of
(a) hydrogen, and
(b) $C_{1-4}$alkyl, each $R^7$ is independently selected from the group consisting of
(a) hydrogen and
(b) $R^8$;

each $R^8$ is independently selected from the group consisting of
(a) $C_{1-6}$alkyl,
(b) phenyl or monosubstituted phenyl wherein the substituents may be halo, $C_{1-4}$alkyl, $C_{1-4}$alkoxy, $C_{1-4}$alkylthio, CN, or $CF_3$,
(c) benzyl or monosubstituted benzyl wherein the substituents may be halo, $C_{1-4}$alkyl, $C_{1-4}$alkoxy, $C_{1-4}$alkylthio, CN, or $CF_3$.

5. A compound according to claim 3 of formula Ib

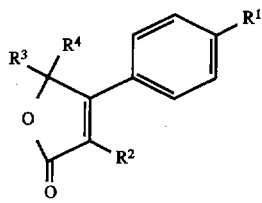
Ib wherein
$R^1$ is selected from the group consisting of
(a) $S(O)_2CH_3$,
(b) $S(O)hd 2NH_2$,
(c) $S(O)hd 2NHC(O)CF_3$,
(d) $S(O)(NH)NH_2$;

$R^2$ is selected from the group consisting of unsubstituted or mono-, di- or tri-substituted phenyl wherein the substituent is selected from the group consisting of
(1) halo,
(2) $C_{1-4}$alkoxy,
(3) $C_{1-4}$alkylthio,
(4) CN,
(5) $CF_3$,
(6) $C_{1-4}$alkyl,
(7) $N_3$,
(8) —$C(R^5)(R^6)$-OH, $R^3$ is hydrogen, $C_{1-4}$alkyl, $CH_2OR^7$, CN, $CH_2CN$, or $C_{1-4}$fluoroalkyl, F, $CONR^7{}_2$;

$R^4$ is
(a) $C_{1-4}$alkoxy,
(b) $C_{1-4}$alkylthio,
(c) —OH,
(d) —$OCOR^7$,
(e) —SH,
(f) —$SCOR^7$,
(g) —$OCO_2R^8$,
(h) —$SCO_2R^8$,
(i) $OCONR^7{}_2$, and
(j) $SCONR^7{}_2$;

each $R^5$ or $R^6$ is independently selected from the group consisting of
(a) hydrogen, and
(b) $C_{1-4}$alkyl, each $R^7$ is independently selected from the group consisting of
(a) hydrogen and
(b) $R^8$;

each $R^8$ is independently selected from the group consisting of
(a) $C_{1-4}$alkyl,
(b) phenyl or monosubstituted phenyl wherein the substituents may be halo, $C_{1-4}$alkyl, $C_{1-4}$alkoxy, $C_{1-4}$alkylthio, CN, or $CF_3$.

6. A compound according to claim 5 of formula Ib

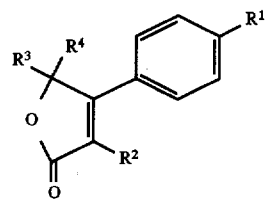
Ib wherein:
$R^1$ is selected from the group consisting of (a) S(O)$_2$CH$_3$,
(b) S(O)$_2$NH$_2$, R$^2$ is selected from the group consisting of unsubstituted or mono-, di- or tri-substituted phenyl wherein the substituent is selected from the group consisting of
(1) halo,
(2) C$_{1-3}$alkoxy,
(3) CF$_3$,
(4) C$_{1-3}$amyl, R$^3$ is hydrogen, C$_{1-3}$alkyl, CH$_2$OR$^7$, C$_{1-4}$fluoroalkyl, F, CONR$^7_2$;

R$^4$ is
(a) C$_{1-3}$alkoxy,
(b) C$_{1-3}$alkylthio,
(c) —OH,
(d) —OCOR$^7$,
(e) —SCOR$^7$,
(f) OCONR$^7_2$, and
(g) SCONR$^7_2$;

each R$^5$ or R$^6$ is independently selected from the group consisting of
(a) hydrogen, and
(b) C$_{1-3}$alkyl, each R$^7$ is independently selected from the group consisting of
(a) hydrogen and
(b) R$^8$;
each R$^8$ is C$_{1-3}$alkyl.

7. A compound according to claim 4 of formula Ib

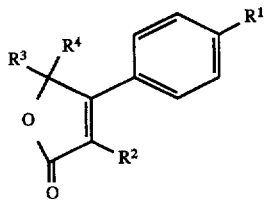

wherein
R$^2$ is a mono or di substituted heteroaryl wherein heteroaryl is selected from the group consisting of
(1) furanyl,
(2) diazinyl, triazinyl, tetrazinyl,
(3) imidazolyl,
(4) isooxazolyl,
(5) isothiazolyl,
(6) oxadiazolyl,
(7) oxazolyl,
(8) pyrazolyl,
(9) pyrrolyl,
(10) thiadiazolyl,
(11) thiazolyl,
(12) thienyl,
(13) triazolyl, and
(14) tetrazolyl,
wherein the substitutents are selected from the group consisting of
(1) hydrogen,
(2) fluoro or chloro,
(3) C$_{1-3}$alkoxy,
(4) C$_{1-6}$alkylthio,
(5) CN,
(6) CF$_3$,
(7) C$_{1-3}$alkyl,
(8) —C(R$^5$)(R$^6$)-OH;
(9) —C(R$^5$)(R$^6$)-O-C$_{1-4}$alkyl.

8. A compound according to claim 7 wherein
R$^2$ is a mono or di substituted heteroaryl wherein heteroaryl is selected from the group consisting of
(1) 2-furanyl,
(2) 3-furanyl,
(3) 2-thienyl,
(4) 3-thienyl,
(5) 3-isoxazolyl,
(6) 4-isoxazolyl,
(7) 5-isoxazolyl,
(8) 3-isothiazolyl,
(9) 4-isothiazolyl,
(10) 5-isothiazolyl,
(11) 2-oxazolyl,
(12) 4-oxazolyl,
(13) 5-oxazolyl,
(14) 2-thiazolyl,
(15) 4-thiazolyl,
(16) 5-thiazolyl,
(17) 1,2,3-thiadiazol-4-yl,
(18) 1,2,3-thiadiazol-5-yl,
(19) 1,2,4-thiadiazol-3-yl,
(20) 1,2,4-thiadiazol-5-yl,
(21) 1,3,4-thiadiazol-2-yl,
(22) 1,2,5-thiadiazol-3-yl,
(23) 1,2,3-oxadiazol-4-yl,
(24) 1,2,3-oxadiazol-5-yl,
(25) 1,2,4-oxadiazol-3-yl,
(26) 1,2,4-oxadiazol-5-yl,
(27) 1,3,4-oxadiazol-2-yl,
(28) 1,2,5-oxadiazol-3-yl,
(29) pyrazol-4-yl,
(30) pyrazol-5-yl,
(31) 1,2,3-triazol-4-yl,
(32) 1,2,3-triazol-5-yl,
(33) 1,2,4-triazol-3-yl,
(34) 1,2,4-triazol-5-yl,
(35) 1,2-diazinyl,
(36) 1,3-diazinyl,
(37) 1,4-diazinyl,
(38) 1,2,3,4-tetrazin-5-yl,
(39) 1,2,4,5-tetrazin-4-yl,
(40) 1,3,4,5-tetrazin-2-yl, and
(41) 1,2,3,5-tetrazin-4-yl.

9. A compound according to claim 8 wherein
R$^2$ is a mono or di substituted heteroaryl wherein heteroaryl is selected from the group consisting of
(1) 3-isoxazolyl,
(2) 4-isoxazolyl,
(3) 5-isoxazolyl,
(4) 3-isothiazolyl,
(5) 4-isothiazolyl,
(6) 5-isothiazolyl,
(7) 2-oxazolyl,
(8) 4-oxazolyl,
(9) 5-oxazolyl,
(10) 2-thiazolyl,
(11) 4-thiazolyl,
(12) 5-thiazolyl,
(13) 1,2,3-thiadiazol-4-yl,
(14) 1,2,3-thiadiazol-5-yl,
(15) 1,2,4-thiadiazol-3-yl,
(16) 1,2,4-thiadiazol-5-yl,
(17) 1,3,4-thiadiazol-2-yl,
(18) 1,2,5-thiadiazol-3-yl,
(19) 1,2,3-oxadiazol-4-yl,
(20) 1,2,3-oxadiazol-5-yl,

(21) 1,2,4-oxadiazol-3-yl,
(22) 1,2,4-oxadiazol-5-yl,
(23) 1,3,4-oxadiazol-2-yl,
(24) 1,2,5-oxadiazol-3-yl,
(25) 1,2-diazinyl,
(26) 1,3-diazinyl, and
(27) 1,4-diazinyl.

10. A compound according to claim 9 wherein the heteroaryl is selected from the group consisting of
(1) 3-isothiazolyl,
(2) 4-isothiazolyl,
(3) 5-isothiazolyl,
(4) 2-oxazolyl,
(5) 4-oxazolyl,
(6) 5-oxazolyl,
(7) 2-thiazolyl,
(8) 4-thiazolyl,
(9) 5-thiazolyl,
(10) 1,2-diazinyl,
(11) 1,3-diazinyl, and
(12) 1,4-diazinyl, and wherein the substitutents are selected from the group consisting of
(1) hydrogen,
(2) fluoro or chloro,
(3) $C_{1-3}$alkoxy,
(4) $C_{1-3}$alkylthio,
(5) CN,
(6) $C_{1-3}$alkyl, and
(7) —C($R^5$)($R^6$)-OH, $R^3$ is hydrogen, $C_{1-4}$alkyl, $CH_2OR^7$, CN, $CH_2CN$, or $C_{1-4}$fluoroalkyl, F, $CONR^7_2$;

$R^4$ is
(a) $C_{1-4}$alkoxy,
(b) $C_{1-4}$alkylthio,
(c) —OH,
(d) —$OCOR^7$,
(e) —SH,
(f) —$SCOR^7$,
(g) —$OCO_2R^8$,
(h) —$SCO_2R^8$;

each $R^5$ or $R^6$ is independently selected from the group consisting of
(a) hydrogen, and
(b) $C_{1-4}$alkyl, each $R^7$ is independently selected from the group consisting of
(a) hydrogen and
(b) $R^8$;

each $R^8$ is independently selected from the group consisting of
(a) $C_{1-4}$alkyl,
(b) phenyl or monosubstituted phenyl wherein the substituents may be halo, $C_{1-4}$alkyl, $C_{1-4}$alkoxy, $C_{1-4}$alkylthio, CN, or $CF_3$.

11. A compound according to claim 10 wherein the hetreoaryl is selected from the group consisting of
(1) 3-isothiazolyl,
(2) 4-isothiazolyl,
(3) 5-isothiazolyl,
(4) 2-oxazolyl,
(5) 4-oxazolyl,
(6) 5-oxazolyl,
(7) 2-thiazolyl,
(8) 4-thiazolyl,
(9) 5-thiazolyl,
(10) 1,2-diazinyl,
(11) 1,3-diazinyl, and
(12) 1,4-diazinyl, and wherein the substitutents are selected from the group consisting of
(1) hydrogen,
(2) fluoro or chloro,
(3) $C_{1-3}$alkoxy,
(4) $C_{1-3}$alkylthio,
(5) CN,
(6) $C_{1-3}$alkyl, and
(7) —C($R^5$)($R^6$)-OH, $R^3$ is $C_{1-3}$alkyl, $CH_2OR^7$, $C_{1-4}$fluoroalkyl, F, $CONR^7_2$;

$R^4$ is
(a) $C_{1-3}$alkoxy,
(b) $C_{1-3}$alkylthio,
(c) —OH,
(d) —$OCOR^7$,
(e) —$SCOR^7$;

each $R^5$ or $R^6$ is independently selected from the group consisting of
(a) hydrogen, and
(b) $C_{1-3}$alkyl, each $R^7$ is independently selected from the group consisting of
(a) hydrogen and
(b) $R^8$;

each $R^8$ is $C_{1-3}$alkyl.

12. A compound selected from the group consisting of
(1) 5-Hydroxy-4-(4-(methylsulfonyl)phenyl)-3-phenyl-2-(5H)-furanone,
(2) 5-Hydroxy-3-(3,4-difluorophenyl)-4-(4-(methylsulfonyl)phenyl)-2-(5H)-furanone,
(3) 5-Hydroxy-5-methyl-4-(4-(methylsulfonyl)phenyl)-3-phenyl-2-(5H)-furanone,
(4) 3-(4-Fluorophenyl)-5-hydroxy-5-methyl-4-(4-(methylsulfonyl)phenyl)-2-(5H)-furanone,
(5) 3-(4-Chlorophenyl)-5-hydroxy-5-methyl-4-(4-(methylsulfonyl)phenyl) -2- (5H)-furanone,
(6) 3-(3,4-Difluorophenyl)-5-hydroxy-5-methyl-4-(4-(methylsulfonyl)phenyl) -2- (5H) -furanone,
(7) 3-(3-Fluorophenyl)-5-hydroxy-5-methyl-4-(4-(methylsulfonyl)phenyl)-2- (5H)-furanone,
(8) 3-(3,5-Difluorophenyl)-5-hydroxy-5-methyl-4-(4-(methylsulfonyl)phenyl) -2- (5H)-furanone,
(9) 5-Methoxy-5-methyl-4-(4-(methylsulfonyl)phenyl)-3-phenyl-2-(5H)-furanone,
(10) 3-(4-Chlorophenyl)-5-methoxy-5-methyl-4-(4-(methylsulfonyl)phenyl)-2-(5H)-furanone,
(11) 3-(3,4-Difluorophenyl)-5-methoxy-5-methyl-4-(4-(methylsulfonyl) phenyl) -2- (5H) -furanone,
(12) 3-(3-Fluorophenyl)-5-methoxy-5-methyl-4-(4-(methylsulfonyl)phenyl)-2-(5H)-furanone,
(13) 3-(3,5-Difluorophenyl)-5-methoxy-5-methyl-4-(4-(methylsulfonyl)phenyl)-2-(5H)-furanone,
(14) 3-(4-Fluorophenyl)-5-methoxy-5-methyl-4-(4-(methylsulfonyl) phenyl)-2-(5H)-furanone,
(15) 5-Ethoxy-3-(4-fluorophenyl)-5-methyl-4-(4-(methylsulfonyl)phenyl)-2-( 5H)-furanone,
(16) 3-(4-Fluorophenyl)-5-methyl-4-(4-(methylsulfonyl) phenyl)-5-propoxy-2-(5H)-furanone, (18) 5-Methyl- 5-methylthio-4-(4-
(17) 3 -(4-Fluorophenyl)-5-isopropoxy-5-methyl-4- (4-(methylsulfonyl)phenyl)-2-(5H)-furanone,

(18) 5-Methyl-5-methylthio-3-(4-(methylsulfonyl)phenyl)-3-phenyl-2-(5H)-furanone,

(19) 5-Ethylthio-5-methyl-4-(4-(methylsulfonyl)phenyl)-3-phenyl-2-(SH)-furanone,

(20) 5-Ethyl-5-hydroxy-4-(4-(methylsulfonyl)phenyl)-3-phenyl-2-(5H)-furanone,

(21) 5-Ethyl-3-(3-fluorophenyl)-5-hydroxy-4-(4-(methylsulfonyl)phenyl)-2-(5H)-furanone,

(22) Acetic acid, 3-(4-(methylsulfonyl)phenyl)-5-methyl-5-oxo-4-phenyl-2,5-dihydrofuran-2-yl ester, and

(23) 5-Hydroxy-5-methyl-4-((4-methylsulfonyl)phenyl)-3-(2-naphthyl)-2-(5H)-furanone.

13. A compound selected from the group consisting of

5-Hydroxy-4-(4-methylsulfonyl)phenyl)-3-phenyl-2-(5H)-furanone,

5-Hydroxy-5-methyl-4-(4-methylsulfonyl)phenyl)-3-phenyl-2-(5H)-furanone, and 3-(4-Chlorophenyl)-5-hydroxy-5-methyl-4-(4-methylsulfonyl)phenyl)-2-(5H)-furanone.

14. A pharmaceutical composition for treating an inflammatory disease susceptable to treatment with an non-steroidal anti-inflammatory agent comprising:

a non-toxic therapeutically effective amount of a compound according to claim 1 and a pharmaceutically acceptable carrier.

15. A pharmaceutical composition for treating cyclooxygenase mediated diseases advantageously treated by an active agent that selectively inhibits COX-2 in preference to COX-1 comprising:

a non-toxic therapeutically effective mount of a compound according to claim 1 and a pharmaceutically acceptable carrier.

16. A method of treating an inflammatory disease susceptable to treatment with an non-steroidal anti-inflammatory agent comprising:

administration to a patient in need of such treatment of a non-toxic therapeutically effective mount of a compound according to claim 1 and a pharmaceutically acceptable carrier.

17. A method of treating cyclooxygenase mediated diseases advantageously treated by an active agent that selectively inhibits COX-2 in preference to COX-1 comprising:

administration to a patient in need of such treatment of a non-toxic therapeutically effective amount of a compound according to claim 1.

18. A method of treating inflammation in a patient for which non-steroidal antiinflammatory drugs may be contraindicated comprising:

administration to a patient in need of such treatment of a non-toxic therapeutically effective amount of a compound according to claim 1 and a pharmaceutically acceptable carrier.

* * * * *